US012584893B2

(12) United States Patent
Agah

(10) Patent No.: US 12,584,893 B2
(45) Date of Patent: Mar. 24, 2026

(54) DEVICES FOR MICRO GAS CHROMATOGRAPHY AND METHODS OF MAKING AND USES THEREOF

(71) Applicant: Virginia Tech Intellectual Properties, Inc., Blacksburg, VA (US)

(72) Inventor: Masoud Agah, Blacksburg, VA (US)

(73) Assignee: VIRGINIA TECH INTELLECTUAL PROPERTIES, INC., Blacksburg, VA (US)

(*) Notice: Subject to any disclaimer, the term of this patent is extended or adjusted under 35 U.S.C. 154(b) by 278 days.

(21) Appl. No.: 17/740,319

(22) Filed: May 9, 2022

(65) Prior Publication Data

US 2022/0373518 A1 Nov. 24, 2022

Related U.S. Application Data

(60) Provisional application No. 63/185,970, filed on May 7, 2021.

(51) Int. Cl.

*G01N 30/14* (2006.01)
*B81B 1/00* (2006.01)

(Continued)

(52) U.S. Cl.

CPC ............. *G01N 30/14* (2013.01); *B81B 1/002* (2013.01); *B81C 1/00071* (2013.01);

(Continued)

(58) Field of Classification Search

CPC .................................................. G01N 30/6095

See application file for complete search history.

(56) References Cited

U.S. PATENT DOCUMENTS

| | | | | | |
|---|---|---|---|---|---|
| 5,116,495 | A * | 5/1992 | Prohaska | G01N 30/6095 210/198.2 |
| 2007/0028668 | A1* | 2/2007 | Goto | G01N 30/32 73/31.05 |
| 2018/0164260 | A1* | 6/2018 | Agah | G01N 30/30 |

OTHER PUBLICATIONS

A. I. Ruiz-Matute, A. C. Soria, I. Martinez-Castro, and M. Sanz, “A new methodology based on GC-MS to detect honey adulteration with commercial syrups,” Journal of agricultural and food chemistry, vol. 55, pp. 7264-7269, 2007.

(Continued)

*Primary Examiner* — John E Breene
*Assistant Examiner* — Alex T Devito
(74) *Attorney, Agent, or Firm* — Perilla Knox & Hildebrandt LLP; Jonathan A. Paulis

(57) ABSTRACT

Micro gas chromatographic devices are provided having a microfluidic separation column and a plurality of capillaries where the capillaries have been independently configured in terms of the capillary length, capillary width, the packing density and packing geometry of the capillary using one or more micro pillars, the tortuosity of the capillary path, and the presence and identity of the stationary phase for use in micro gas chromatographic separation of complex mixtures of compounds. Through the plurality of capillaries, the devices are capable of discriminating between complex samples even in instances where complete separation of the components is not possible. Methods of fabrication and methods of use of the devices are also provided. The devices can be readily fabricated using known techniques. The devices can be used for the analysis of complex mixtures of compounds containing tens or hundreds of compounds in which just a few differ in presence or concentration.

20 Claims, 22 Drawing Sheets

(51) Int. Cl.
*B81C 1/00* (2006.01)
*G01N 30/30* (2006.01)
*G01N 30/62* (2006.01)
*G01N 33/00* (2006.01)
*G01N 30/02* (2006.01)

(52) U.S. Cl.
CPC ............ *G01N 30/30* (2013.01); *G01N 30/62* (2013.01); *G01N 33/0047* (2013.01); *B81B 2201/0214* (2013.01); *B81B 2203/0338* (2013.01); *B81C 2201/0132* (2013.01); *B81C 2201/0198* (2013.01); *B81C 2203/031* (2013.01); *G01N 2030/025* (2013.01)

(56) References Cited

OTHER PUBLICATIONS

B. P. Regmi, J. Monk, B. El-Zahab, S. Das, F. R. Hung, D. J. Hayes, et al., "A novel composite film for detection and molecular weight determination of organic vapors," Journal of Materials Chemistry, vol. 22, pp. 13732-13741, 2012.

C. F. Poole and S. K. Poole, "Ionic liquid stationary phases for gas chromatography," Journal of separation science, vol. 34, pp. 888-900, 2011.

D. W. Armstrong, L. He, and Y.-S. Liu, "Examination of ionic liquids and their interaction with molecules, when used as stationary phases in gas chromatography," Analytical chemistry, vol. 71, pp. 3873-3876, 1999.

H. Shakeel and M. Agah, "High-Performance Multicapillary Gas Separation Columns with MPG Stationary Phases," 2011 Jeee Sensors, pp. 1909-1912, 2011.

H. Shakeel, D. Wang, R. Heflin, and M. Agah, "Width-modulated microgas chromatography separation cols. with silica nanoparticles stationary phase," 2013 Jeee Sensors, pp. 8-11, 2013.

J. Ding, T. Welton, and D. W. Armstrong, "Chiral ionic liquids as stationary phases in gas chromatography," Analytical chemistry, vol. 76, pp. 6819-6822, 2004.

J. L. Anderson and D. W. Armstrong, "Immobilized ionic liquids as high-selectivity/high·temperature/high-stability gas chromatography stationary phases," Analytical chemistry, vol. 77, pp. 6453-6462, 2005.

J. L. Anderson, J. Ding, T. Welton, and D. W. Armstrong, "Characterizing ionic liquids on the basis of multiple solvation interactions," Journal of the American Chemical Society, vol. 124, pp. 14247-14254, 2002.

J. L. Anderson, R. Ding, A. Ellern, and D. W. Armstrong, "Structure and properties of high stability geminal dicationic ionic liquids," Journal of the American Chemical Society, vol. 127, pp. 593-604, 2005.

J. V. Seeley, S. K. Seeley, E. K. Libby, Z. S. Breitbach, and D. W. Armstrong, "Comprehensive two-dimensional gas chromatography using a high-temperature phosphonium ionic liquid column," Analytical and bioanalytical chemistry, vol. 390, pp. 323-332, 2008.

M. D. Joshi and J. L. Anderson, "Recent advances of ionic liquids in separation science and mass spectrometry," Rsc Advances, vol. 2, pp. 5470-5484, 2012.

M. H. Abraham, "Scales of solute hydrogen-bonding: their construction and application to physicochemical and biochemical processes," Chemical Society Reviews, vol. 22, pp. 73-83, 1993.

M. Qi and D. W. Armstrong, "Dicationic ionic liquid stationary phase for GC-MS analysis of volatile compounds in herbal plants," Analytical and bioanalytical chemistry, vol. 388, pp. 889-899, 2007.

M. Stadermann, A. D. McBrady, B. Dick, V. R. Reid, A. Noy, R. E. Synovec, et al., "Ultrafast gas chromatography on single-wall carbon nanotube stationary phases in microfabricated channels," Analytical Chemistry, vol. 78, pp. 5639-5644, Aug. 15, 2006.

P. Berton, B. P. Regmi, D. A. Spivak, and I. M. Warner, "Ionic liquid-based dispersive microextraction of nitrotoluenes in water samples," Microchimica Acta, vol. 181, pp. 1191-1198, 2014.

S. Narayanan, B. AJfeeli, and M. Agah, "Two-Port Static Coated Micro Gas Chromatography col. With an Embedded Thermal Conductivity Detector," Ieee Sensors Journal, vol. 12, Jun. 2012.

Wang, A. Muhammad, J. R. Heflin, and M. Agah, "Novel Layer-by-Layer Silica Nanoparticles as an adorbent bed for Microfabricated Preconcentrators," 2012 IEEE Sensors Proceedings, pp. 119-122, 2012.

* cited by examiner

| | |
|---|---|
| ① | Wafer handle layer / Device layer |
| ② | Lithography - Mask layer patterning |
| ③ | DRIE etch |
| ④ | Anodic bonding |

- Glass/ pyrex
- Si wafer
- Masking layer.
- SIO2 layer

| | |
|---|---|
| ① | Bare Si wafer |
| ② | Bonded silicon wafer and glass |
| ③ | Lithography - Mask layer patterning |
| ④ | DRIE etch |
| ⑤ | Anodic bonding |

- Glass/ pyrex
- Si wafer
- Masking layer. Can be Photoresist, Oxide or metal.

DEVICES FOR MICRO GAS CHROMATOGRAPHY AND METHODS OF MAKING AND USES THEREOF

CROSS-REFERENCE TO RELATED APPLICATIONS

This application claims priority to, and the benefit of, co-pending U.S. provisional application entitled "FOX ON A CHIP FOR RAPID CHEMICAL ANALYSIS" having Ser. No. 63/185,970 filed May 7, 2021, the contents of which are incorporated by reference herein.

TECHNICAL FIELD

The present disclosure generally relates to devices for micro gas chromatography and methods of making and uses thereof.

BACKGROUND

Volatile organic compounds (VOCs) constitute a large group of organic chemicals that evaporate easily under normal conditions of temperature and pressure. VOCs are emitted in the atmosphere from a wide variety of natural and anthropogenic sources. The natural sources of VOCs are plants, animals, natural forest fires, and anaerobic processes in certain natural environments. The major human activities that release VOCs include transportation, industrial activities, biomass burning, solvent use, and agricultural activities [1-3]. The biogenic emissions of VOCs are much greater than the anthropogenic emissions. At the global level, approximately 1300 Tg of carbon per year in the form of VOCs is emitted; the biogenic emission accounts for 1150 Tg of C/year, while anthropogenic emission accounts for 142 Tg of C/year [4]. It is quite surprising that more than 1000 VOCs containing only one carbon atom may be found in the atmosphere [4]. Some VOCs have no adverse health effects, while some are toxic and/or carcinogenic [5]. The characterization and monitoring of VOCs emitted from different sources is immensely important in different disciplines ranging from biomedical diagnostics, homeland security, food safety and quality, and environmental protection.

Different analytical instruments for detecting volatile analytes can be categorized into two general approaches. The first approach measures the analyte in place without the need for isolation; whereas the second approach first separates the gaseous mixture into its constituents and then analyzes them individually.

Electronic noses (e-nose) are considered to be in the first category. They typically include a sensor array with partially overlapping selectivity where each sensor displays different sensitivities to different vapors. E-noses have an appropriate pattern recognition algorithm which is trained by introducing different known chemicals to the system. The obtained patterns are then used by the electronic nose to process and identify gases in the mixture [1, 2]. While e-noses have the potential to combine high throughput and ease of use with low cost [3-5], they are not suitable for identification of complex gas mixtures.

The second set of methods include gas chromatography (GC), gas chromatography coupled to mass spectrometry (GC-MS), and ionic mobility spectrometry (IMS) [6-8]. GC-MS instrumentation is expensive, bulky, and requires skilled workers for operation. Although, IMS is simple, sensitive and selective, it suffers from a number of limitations including ease of contamination, low resolution, narrow dynamic range, long residence time, and competitive ion-molecule reactions [8]. Therefore, conventional GC and has been the most common approach for analysis of complex gaseous mixtures. GC systems normally consist of a carrier gas tank, a sample injector, a separation column, and a detector. While the gas mixture travels through the column in an inert mobile phase (carrier gas), molecules will spend different amounts of time in the stationary-phase coating due to variations in intermolecular interactions and volatility so that compounds emerge from the column at different times. The gases then pass through a detector, producing an electronic signal proportional to the concentrations of the different components. The retention time (delay time between injection and detection) of each individual compound eluting from the column can be used for identification. Conventional GC columns may be capable of resolving complex mixtures of VOCs due to the long (~15-30 m) columns employed. However, the long column lengths also lead to increased expense, a lack or portability, and long sample testing times—all of which are a drawback for making widely applicable, portable, and inexpensive solutions for use in the field. To solve these problems, recent advances in the development of microfabricated gas chromatograms (μGCs) have brought the powerful analytical technique to the field. However, as the sample complexity increases, the full separation of all analytes using MEMS-enabled microfabricated gas chromatogram columns becomes more challenging as these columns are typically 50 cm-2 m long and are unable of separating the complex mixtures of VOCs.

There remains a need for improved devices capable of analyzing samples containing complex mixtures of VOCs.

There further remains a need for inexpensive and easy to fabricate devices capable of analyzing samples containing complex mixtures of VOCs.

There also remains a need for methods of analyzing complex mixtures of VOCs that are both fast and reliable.

SUMMARY OF THE DISCLOSURE

Micro gas chromatographic devices are provided for rapid detection of volatile organic compounds in a sample containing a plurality of volatile organic compounds. The devices can include a microfluidic separation column with a column inlet; a plurality of capillaries, wherein each of the capillaries in the plurality of capillaries is independently in fluid communication with the microfluidic separation column at a capillary inlet, and wherein each of the capillaries in the plurality of capillaries has a capillary outlet opposite the capillary inlet; and a plurality of micro-detectors, wherein each of the micro-detectors in the plurality of micro-detectors is independently positioned at or near the outlet of a capillary in the plurality of capillaries and configured to detect one or more volatile organic compounds passing through the capillary.

Methods of making a gas chromatographic device are also provided. The methods can include applying a photoresist layer to a first surface of a silicon wafer to produce a mask layer; patterning the mask layer using photolithography to produce a patterned mask layer defining at least the microfluidic separation column and plurality of capillaries; etching the silicon wafer having the patterned mask layer to produce an etched silicon wafer; recleaning the etched silicon wafer; and bonding a lid on the surface of the etched silicon wafer to form the microfluidic separation column and the plurality of capillaries.

Methods are provided for detecting one or more volatile organic compounds from a sample comprising a plurality of volatile organic compounds. The methods can include causing the sample to flow into the column inlet of a micro gas chromatographic device according to claim 1, whereby each of the volatile organic compounds flows into one or more of the capillary inlets; and measuring a signal at one or more of the detectors in plurality of micro-detectors, wherein the one or more signals produced by the one or more detectors is indicative of a presence or an absence of a volatile organic compound in the plurality of volatile organic compounds.

Other aspects, modifications, uses, and advantages of the micro gas chromatographic devices, methods of making, and methods of use will be apparent to those skilled in the art upon reading the following disclosure.

BRIEF DESCRIPTION OF THE DRAWINGS

Further aspects of the present disclosure will be readily appreciated upon review of the detailed description, described below, when taken in conjunction with the accompanying drawings.

FIGS. 9A-9B are graphs of the gas chromatographic detector signal as a function of time for three different diesel concentrations of 90%, 95%, and 100% (v/v) for Phase A and Phase B respectively. Figures of merit (FOM) of the Partial Least Squares Regression (PLSR) method are provided in the insets of FIGS. 9A-9B. Both Phase A and B show R2-P values greater than 0.9, affirming that the model can predict adulteration content accurately. FIGS. 9C-9D are the graphs of the Root mean squared error of cross validation (RMSECV) and root mean squared error of prediction (RMSEP) as a function of the number of principal components for Phase A and Phase B respectively.

FIGS. 10A-10B are graphs of the gas chromatographic detector signal as a function of time for three different diesel concentrations of 90%, 95%, and 100% (v/v) for Phase A and Phase B respectively. Figures of merit (FOM) of the Partial Least Squares Regression (PLSR) method are provided in the insets of FIGS. 10A-10B. Phase A and B show RMSEP values ~0.5% (v/v) and R2-P over 0.9 demonstrating both models are effectively able to predict the adulteration content. FIGS. 10C-10D are the graphs of the Root mean squared error of cross validation (RMSECV) and root mean squared error of prediction (RMSEP) as a function of the number of principal components for Phase A and Phase B respectively.

FIGS. 11A-11B are graphs of the gas chromatographic detector signal as a function of time for three different diesel concentrations of 90%, 95%, and 100% (v/v) for Phase A and Phase B respectively. Figures of merit (FOM) of the Partial Least Squares Regression (PLSR) method are provided in the insets of FIGS. 11A-11B. The R2-P was also low (0.032) indicating inability of the model to predict adulteration percentage with only 4 s of data. Phase B shows RMSEP of 1.012% (v/v) and an R2-P value greater than 0.9 which shows the model can predict the adulteration content with 4 s of data. FIGS. 11C-11D are the graphs of the Root mean squared error of cross validation (RMSECV) and root mean squared error of prediction (RMSEP) as a function of the number of principal components for Phase A and Phase B respectively.

DETAILED DESCRIPTION

Figure 1:
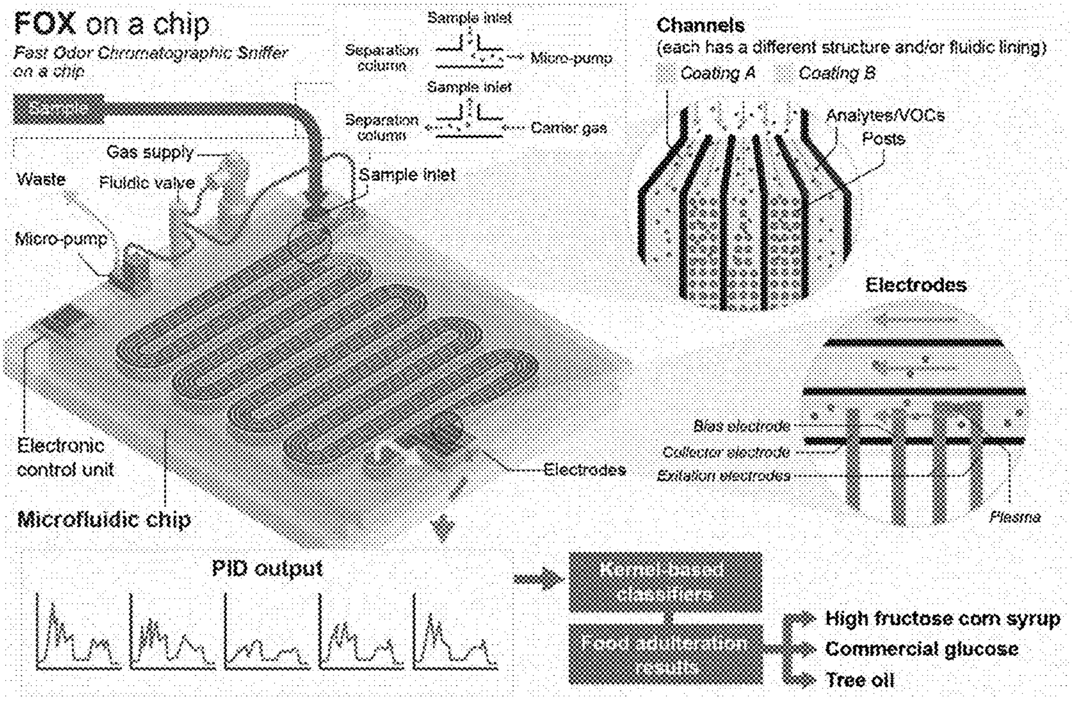
FIG. 1 is a schematic of an exemplary fast chromatographic sniffer implemented using multi-channel fast micro gas chromatography and electronic noses.

In various aspects described herein are micro gas chromatographic devices that overcome one or more of the aforementioned deficiencies. Further, in various aspects described herein are methods of making micro gas chromatographic devices. Also described in various aspects herein are methods that are both fast and reliable for using gas chromatographic devices to analyze complex mixtures of VOCs.

Other systems, methods, features, and advantages of devices and methods will be or become apparent to one with skill in the art upon examination of the following drawings and detailed description. It is intended that all such additional systems, methods, features, and advantages be included within this description, be within the scope of the present disclosure, and be protected by the accompanying claims.

Although any methods and materials similar or equivalent to those described herein can also be used in the practice or testing of the present disclosure, the preferred methods and materials are now described. Functions or constructions well-known in the art may not be described in detail for brevity and/or clarity. Aspects of the present disclosure will employ, unless otherwise indicated, techniques of microfluidics, photolithography, gas chromatography, nanotechnology, organic chemistry, material science and engineering and the like, which are within the skill of the art. Such techniques are explained fully in the literature.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant specification should not be treated as such and should not be read as defining any terms appearing in the accompanying claims. Furthermore, any incorporation by reference of patents and patent applications to which the instant application claims priority is not intended to extend to any lexicographical definitions in the patents and patent applications so incorporated and should not be read as limiting the accompanying claims.

The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to about 5%" should be interpreted to include not only the explicitly recited values of about 0.1% to about 5%, but also include individual values (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g., the phrase "x to y" includes the range from 'x' to 'y' as well as the range greater than 'x' and the range less than 'y'. The range can also be expressed as an upper limit e.g., 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In some aspects, the term "about" can include traditional rounding according to significant figures of the numerical value. In addition, the phrase "about 'x' to 'y'", where 'x' and 'y' are numerical values, includes "about 'x' to about 'y'".

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The articles "a" and "an," as used herein, mean one or more when applied to any feature in aspects of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

Micro Gas Chromatographic Devices

In various aspects, micro gas chromatographic devices are provided. As described more fully below, the micro gas chromatographic devices can be made inexpensively and with a variety of column designs and enable methods that can quickly and reliably analyze complex mixtures of volatile organic compounds.

The chromatographic devices include one or more microfluidic separation columns having a column inlet where a sample to be analyze can enter the column. There are various approaches for introducing the sample into the column inlet e.g., using a syringe, through active or passive diffusion into the system, or through using an injection port assembly substantially as described herein. As depicted in FIG. 1, the micro gas chromatographic device can include a micro-pump to controllably pump a carrier gas into the system to introduce the sample. The micro-pump can be in fluid communication with the column inlet. In some aspects, the micro-pump is also in fluid communication with a sample port. The sample port can be configured to receive a sample or a portion thereof containing VOCs to be analyzed. In some aspects, the micro-pump can be configured to pull or draw the sample into the sample port in a first setting. In some aspects, a second setting on the micro-pump causes the portion of the sample in the sample port to be introduced into the column inlet and to be carried through the column using the carrier gas.

The micro gas chromatographic device includes a microfluidic separation column having a plurality of capillaries. The micro gas chromatographic devices can further include various stationary phases and micro detectors useful for analyzing the complex mixtures of VOCs. The micro gas chromatographic devices can further include other components such as control circuitry, heaters for controlling the temperature, temperature sensors.

The microfluidic separation column includes a plurality of capillaries. Each of the capillaries in the plurality of capillaries is independently in fluid communication with the microfluidic separation column at a capillary inlet, and each of the capillaries in the plurality of capillaries has a capillary outlet opposite the capillary inlet. It is believe that the plurality of capillaries provide for enhanced resolution and ability to rapidly identify and analyze complex mixtures of VOCs in an efficient manner. The microfluidic separation column can include a large number of capillaries e.g., from about 2, 3, 4, 5, 6, 7, 8, 9, or 10 capillaries and up to about 20, 25, 30, 40, 50, or 100 capillaries or more.

The capillaries can each be configured differently so as to provide for different detector profiles for a given sample, which improves the speed and the reliability by which the complex samples can be analyzed. Each of the capillaries can be distinct in terms of one or more variables including the capillary length, capillary width, with or without micropillars in varying configurations, with distinct stationary phases, a tortuosity of the capillary, and/or with distinct micro detectors.

The capillary length can be adjusted to improve the reliability of separating the VOCs. For example, in some aspects increasing the capillary length can lead to increased separation of the complex mixtures of VOCs. However, there can be a tradeoff between capillary length and the speed of detection. In some instances, because a plurality of capillaries are being used the length of the capillary can be shorter to favor increased speed of detection. In some instances, the length of the capillaries can be decreased while maintaining the accuracy and improving the speed simply by increasing the number of capillaries. In some instances, the capillaries have a capillary length of about 5, 10, 20, 25, 50, 75, or 100 cm and up to about 50 cm, 100 cm, 1.5 m, 2.0 m, 2.5 m, or more.

The capillary width can be adjusted to improve the separation efficiency. In some aspects, the width of the capillary can be relatively narrow. In some aspects, capillary width can be from about 10 μm, 20 μm, 30 μm, 40 μm, 50 μm, 75 μm, 100 μm and up to about 100 μm, 200 μm, 300 μm, 400 μm, 500 μm, 750 μm, 1000 μm, or more.

Within each capillary, two additional variables that can be controlled include the geometrical features and the coating. The geometry can include a plurality of pillars within the column. The pillars can be arranged in open rectangular, semi-packed, or density-modulated semi-packed capillaries (DMSPC). The design of μGC columns in general and semi-packed columns in particular can play an important factor in the separation performance. For very thin stationary phase films, the mass transfer in the mobile phase is the main contributor to band broadening. The band broadening can be diminished by reducing the mass transfer distances and maintaining a constant velocity across the column width. In some instances, this can be achieved by columns with integrated microposts having narrow spacings between them. More specifically, the positioning of pillars inside the micro channel has shown to affect the velocity profile, and pressure distribution. It is believed that the staggered leads to improvements in the mass-transfer and enhancement of the separation efficiency. Moreover, the staggered pillar design can in some aspects enhance the resolution and sample capacity as the interaction of molecules with the column surface is enhanced. By varying the packing densities along the column length, pressure drop requirements can be reduced (in contrast to a highly packed column) and thereby enhance the sample capacity (in contrast to lightly packed columns).

In some aspects, the array of micropillars has a geometry with a semi-packed architecture, which can be staggered or unstaggered. In some aspects, the pillars have a pitch size from about 1 μm, 2 μm, 3 μm, 4 μm, 5 μm, 6 μm, 7 μm, 8 μm, 9 μm, 10 μm and up to about 10 μm, 20 μm, 30 μm, 40 μm, 50 μm or more. In some aspects, the pillars have a row spacing of about 1 μm, 2 μm, 3 μm, 4 μm, 5 μm, 6 μm, 7 μm, 8 μm, 9 μm, 10 μm and up to about 10 μm, 20 μm, 30 μm, 40 μm, 50 μm or more.

In some aspects, the capillary includes no stationary phase and simply relies upon the geometry to facilitate separation. In some aspects, the capillary includes a stationary phase to interact with the VOCs passing through the capillary and facilitate separation. The stationary phase can include conventional stationary phases used for gas chromatography. The stationary phase can include polyunsaturated hydrocarbons such as squalene. The stationary phase can include petroleum based greases such as petrolatum hydrocarbon greases. The stationary phase can include polysiloxanes such as polydimethyl siloxane, phenylmethyl polysiloxane, trifluoropropylmethyl polysiloxane, and trifluoropropylmethyl polysiloxane. The stationary phase can include polyalkylene glycols such as polyethylene glycol and polypropylene glycol. The stationary phase can include gold nanoparticles or other nanoparticles. The stationary phase can include silica nanoparticles. The stationary phase can include alumina. The stationary phase can include ionic liquids such as 1-Butyl-3-methylimidazolium hexafluorophosphate, 1-Butyl-3-methylimidazolium bis(trifluoromethylsulfonyl)imide, trihexyltetradecyl-phosphonium bis(trifluoromethylsulfonyl)imide, 1-butylpyridinium bis (trifluoromethylsulfonyl)imide, trihexyl(tetradecyl) phosphonium bis[(trifluoromethyl)sulfonyl]imide, and trihexyl(tetradecyl)phosphonium chloride. The stationary phase can include metal organic frameworks. The stationary phase can include compounds having a structure according to the following formula

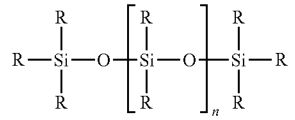

wherein n is an integer from about 1, 2, 3, 4, 5, and up to about 10, 20, 30, 40, 50, 100, or more. In each instance above, each occurrence of R can be independently selected from the group consisting of methyl, ethyl, phenyl, trifluoropropyl, —$C_3H_6CF$, cyanopropyl, and —$C_3H_6CN$; and stationary phases comprising a combination of the above.

The micro gas chromatographic device includes one or more micro detectors. Suitable micro detectors are known in the literature, many of which can be readily utilized or adapted for use in the devices described herein, Suitable micro detectors can include of a pTCD detector, a pFID detector, a MOS gas sensor, a capacitive detector, a MPN chemiresistor, a SAW detector, a pPID detector, a pPlasma ionization detector, or a combination thereof. Suitable micro detectors can include those described in Qu, H., & Duan, X. (2019). Recent advances in micro detectors for micro gas chromatography. *Science China Materials,* 62(5), 611-623.

| Detector | Portable GC instrumentation | Comments on the detectors | Reference |
|---|---|---|---|
| μTCD | Carrier gas: helium; hydrogen; nitrogen; argon<br>Column: capillary column<br>Size and weight [81]: 15 cm × 45 cm × 30 cm, ~3.5 kg<br>Size and weight [23]: 46.2 cm × 19.6 cm × 25.4 cm, ~6.2 kg<br>Power: 100-240 V | Concentration sensitive and universally responsive; good linearity; detection limit comparable with conventional TCD; no need for auxiliary gas; relatively easy to miniaturize; good candidate for handheld GC | [23, 81] |
| μFID | Carrier gas: electrolyzed for the generation of $H_2$ and $O_2$<br>Column: MEMS silicon column<br>Size and weight: 24 cm × 20 cm × 10 cm, ~4 kg<br>Power: Li-ion battery | Mass sensitive with little/no response to inflammable gases; good linearity; detection limit inferior to that of conventional FID; needs auxiliary gas; difficult to miniaturize; challenging for use in handheld GC | [7] |

-continued

| Detector | Portable GC instrumentation | Comments on the detectors | Reference |
|---|---|---|---|
| MOS gas sensor ($SnO_2$) | Carrier gas: synthetic air<br>Column: MEMS silicon column with concentrator<br>Size and weight: NA;<br>Power: NA | Concentration sensitive with tunable selectivity; nonlinearity; detection limit down to sub-ppm; no need for auxiliary gas; easy to miniaturize; mass produced; good candidate for handheld GC | [59] |
| Capacitive detector | Carrier gas: purified air<br>Column: capillary column<br>Size and weight: 10.8 cm × 13.3 cm × 19.1 cm, ~1.3 kg<br>Power: 100-240 V AC power supply | Concentration sensitive with tunable selectivity; good linearity; detection limit down to ppm; no need for auxiliary gas; easy to miniaturize; mass produced; good candidate for handheld GC | [54, 82] |
| MPN chemiresistor | Carrier gas: purified air<br>Column: MEMS silicon column with concentrator<br>Size and weight [71]: 44 cm × 25.5 cm × 14.5 cm, ~4.5 kg<br>Size and weight [70]: 16 cm × 11 cm × 11 cm, NA<br>Power: main AC power supply | Concentration sensitive with tunable selectivity; good linearity; detection limit down to sub-ppm; no need for auxiliary gas; easy to miniaturize; good candidate for handheld GC | [70, 71] |
| SAW | Carrier gas: helium<br>Column: capillary column<br>Size and weight: 31.8 cm × 26.4 cm × 14.5 cm, ~8.5 kg<br>Power: battery | Concentration sensitive with tunable selectivity; good linearity; detection limit down to ppm; no need for auxiliary gas; easy to miniaturize; mass produced; good candidate for handheld GC | [31] |
| μPID | Carrier gas: scrubbed ambient air<br>Column: NA<br>Size and weight: 28 cm × 20 cm × 30 cm, ~2.2 kg<br>Power: battery | Mass sensitive; applicable in aromatic hydrocarbon anaylsis; good linearity; detection limit comparable with that of the bulk device; no need for auxiliary gas; needs light source; difficult to miniaturize; challenging to use in handheld GC | [27, 83] |
| μPlasma ionization detector | Carrier gas: helium<br>Column: semipacked MEMS silicon column<br>Size and weight: NA<br>Power: NA | Mass sensistive; good linearity; detection limit comparable with that of the bulk device; needs auxiliary gas; difficult to miniaturize; challenging to use in handheld GC | [44] |

References in the table above from Qu, H., & Duan, X. (2019). Recent advances in micro detectors for micro gas chromatography. *Science China Materials,* 62(5), 611-623.

The micro gas chromatographic devices can be made with a printed circuit board for electronic control circuitry. The circuit board can include a power management unit. In some aspects, for example where plasma generation is needed for detectors, the port management unit can include a power generator capable of generating the high voltage (500V, 20 μA) required for plasma generation through a DC-DC converter or through an on-board micropower high voltage power supply. The on-chip heater and sensor as well as the digital control system can also be included. For interfacing, the device can include signal conditioning and a high-precision analog-to-digital converter. The signal-to-noise ratio can be optimized by tuning the amplifier gain, digital filter characteristics, and cut-off frequency. This can allow high sensitivity at an acquisition rate of 10-100 Hz. The board can have a plurality of such units (e.g., five such units) multiplexed over serial peripheral interface (SPI) of a microcontroller. An on-board storage (e.g., a microSD card) can also be provided for data-logging, enhancing stand-alone capabilities of the system. For real-time visualization and analysis of the chromatographs, a wireless interface (e.g., a Bluetooth interface) can be provided for wireless communication with mobile platforms.

Methods of Making Micro Gas Chromatographic Devices

Provided herein are methods of making the micro gas chromatographic devices. The methods will include, in many aspects, methods that are known in the field of lithography, microfluidics design and manufacturing, gas chromatography, and the like which are described elsewhere in the literature. Of particular significance for the current methods, methods are described herein for fabricating the micro gas chromatographic devices having a plurality of capillaries as described herein. The methods can facilitate manufacture of the devices, and in particular in the manufacture of devices with precisely controlled dimensions of the capillaries.

The devices can in principle be made using any methods known in the art of making microfluidic devices so long as such methods are capable of producing the precise geometries needed. In some aspects, the methods include (a) applying a photoresist layer to a first surface of a silicon wafer to produce a mask layer; (b) patterning the mask layer using photolithography to produce a patterned mask layer defining at least the microfluidic separation column and plurality of capillaries; (c) etching the silicon wafer having the patterned mask layer to produce an etched silicon wafer; (d) recleaning the etched silicon wafer; and € bonding a lid on the surface of the etched silicon wafer to form the microfluidic separation column and the plurality of capillaries.

Figure 2:
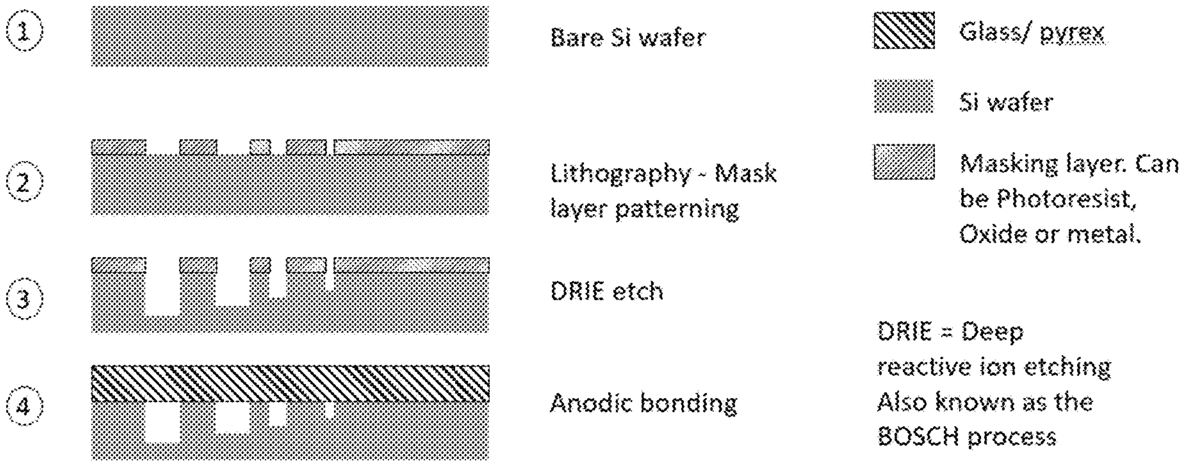
FIG. 2 is a schematic depicting an exemplary process of fabricating multi-channel micro gas chromatographic devices.

In some methods, as depicted in FIG. 2, the depth of the columns in the wafer is controlled by timing the etch duration of the DRIE process to attaining a specific etch depth. The etch depth is thus dependent on the etch rate of the specific DRIE system and factors within the system. A calibration step to determine the etch rate is usually necessary before the etch step. The etch rate not only differs for different systems but can also change depending of the status of the system. In some aspects method comprises in step (c) timing the etching to control a depth of the microfluidic separation column and plurality of capillaries.

Figure 3:
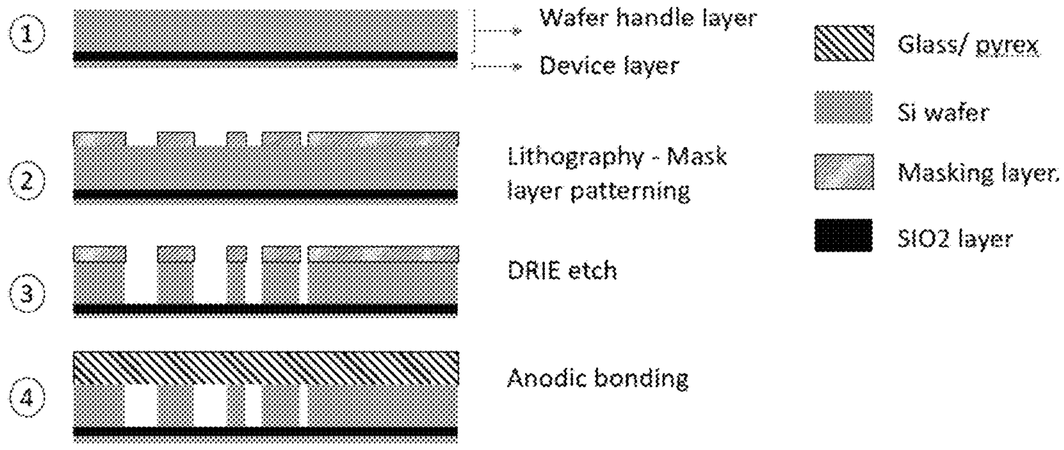
FIG. 3 is a schematic depicting an exemplary process of fabricating multi-channel micro gas chromatographic devices.

In some instance, as depicted in FIG. 3, the depth of the columns in the wafer is controlled by fabrication on silicon on insulator (SOI) wafer. SOI wafer are typically characterized by three different layers: 1) handle, 2) SiO2 and 3) device layer. The methods can include using the handle layer for fabrication of out MEMS separation columns and other associated devices required for the system such as preconcentrators, detectors, etc. After patterning the masking layer. The DRIE etch process then etches the silicon for creating the device trenches. Silicon dioxide ($SIO_2$) serves as an etch-stop for the DRIE process. This makes the depth of the trench independent of the etch rate and dependent of the wafer thickness. In some aspects, the silicon wafer comprises a silicon-on-insulator wafer comprising at least a wafer handle layer and a silicon oxide layer, and the method comprises in step (c) etching the wafer handle layer until reaching the silicon oxide layer to control a depth of the microfluidic separation column and plurality of capillaries.

Figure 4:
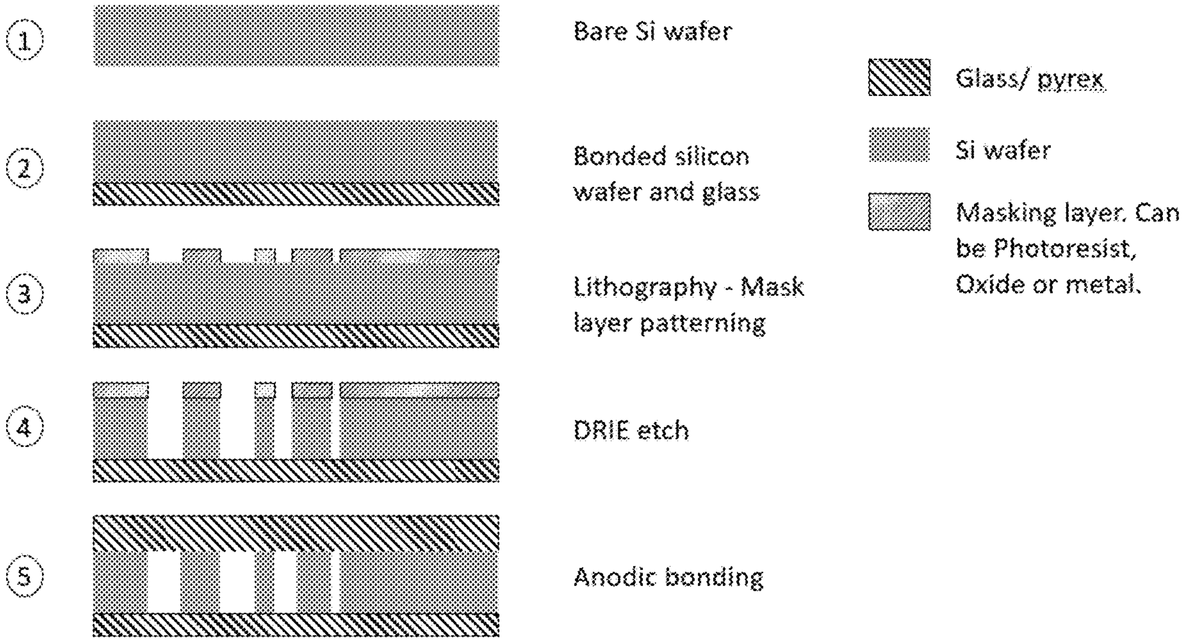
FIG. 4 is a schematic depicting an exemplary process of fabricating multi-channel micro gas chromatographic devices.

In some instances, as depicted in FIG. 4, the depth of the columns in the wafer is controlled by fabrication on Glass-Si-Glass wafer. Glass primarily composed of $SiO_2$ is also an etch stop layer for the DRIE process. The methods can include bonding the glass layer to one side of the silicon wafer for it to act as an etch stop layer. After patterning the masking layer the DRIE etch process etches the silicon for creating the device trenches. Silicon dioxide ($SIO_2$) serves as an etch-stop for the DRIE process. This makes the depth of the trench independent of the etch rate and dependent of the wafer thickness. In some aspects, the method further comprises a step (a') prior to step (c), step (a') comprising bonding a glass or pyrex layer to a second surface of the silicon wafer opposite the first surface; and wherein the method comprises in step (c) etching the wafer to the glass or pyrex layer to control a depth of the microfluidic separation column and plurality of capillaries.

The methods can include functionalizing one or more capillaries with a different stationary phase by pumping each if the different stationary phases into a different outlet in the plurality of capillary outlets. Any of the stationary phases described herein can be introduced into an outlet in the plurality of outlets to coat the respective channel. In some instances the stationary phase is first mixed with a suitable solvent prior to coating. The solvent can be removed by drying the capillaries e.g., by pumping a dry gas through the capillaries.

Methods of Using Micro Gas Chromatographic Devices

The micro gas chromatographic devices can be used for analyzing VOCs in a wide variety of complex samples efficiently and reliably. In some instances, the methods include analyzing petroleum products, fuels, gasoline, kerosene, diesel and the like e.g., analyzing for specific additives or impurities. In some aspects, the methods can include analyzing breath of humans or non-human mammals to detect various things such as disease or health state, blood alcohol content, or the like. The methods can be used to detect airborne toxins, chemical agents, or the like. The methods can be used to detect dangerous airborne pathogens. The methods can be used for detection of food spoiling or contamination. The methods can include applications ranging from biomedical diagnostics, homeland security, food safety and quality, and environmental protection.

The methods can include optimizing the micro Gas chromatography separation column efficiency, resolution, sample capacity and selectivities by their design and geometry. They can also include optimizing the temperature programming and pressure conditions. The methods can utilize a wide selection of column geometries in combination of factors such as temperature programming and pressure and functionalization techniques for creating the different patterns for identification of the various chemical compounds.

In some aspects, the methods can include detecting one or more volatile organic compounds from a sample comprising a plurality of volatile organic compounds. The method can include (a) causing the sample to flow into the column inlet of a micro gas chromatographic device according to claim 1, whereby each of the volatile organic compounds flows into one or more of the capillary inlets; (b) measuring a signal at one or more of the detectors in plurality of micro-detectors, wherein the one or more signals produced by the one or more detectors is indicative of a presence or an absence of a volatile organic compound in the plurality of volatile organic compounds.

In some aspects, the micro gas chromatographic device includes a sample port in fluid commination with a micro-pump and in fluid communication with the column inlet. The method can include placing the micro-pump in a first setting to draw a portion of the sample into the sample port. The method can further include placing the micro-pump in a second setting to inject the portion of the sample into the column inlet.

The methods can further include controlling one or more of a pressure and/or a flow rate of a carrier gas flowing into the column inlet, a temperature of a capillary in the plurality of capillaries, and a time period during which signals are detected at the one or more detectors.

The method can include one or more of (i) a principal component analysis and (ii) a partial least squares regression over the signals from the one or more detectors for a period of time from 5 minutes, about 3 minutes, about 2 minutes, about 1 minute, about 30 seconds, about 10 seconds, about 5 seconds or less.

The methods can be useful to distinguish complex mixtures of compounds (e.g., 50, 70, or 100 compounds for instance) from each other when only a few (e.g., 1, 2, 3, 4, 5, or 6) analytes would be different between different samples.

REFERENCES

The present disclosure will be better understood upon review of the following publications, each if which is incorporated by reference herein. Such incorporation by reference is expressly limited to the methods and/or materials described in the cited publications and patents and does not extend to any lexicographical definitions from the cited publications and patents. Citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

[1] J. Ouellette. (1999, February) Electronic noses sniff out new markets. *The Industrial Physicist Magazine.* 26-29.

[2] P. E. Keller, L. J. Kangas, L. H. Liden, S. Hashem, and R. T. Kouzes, "Electronic noses and their applications," in *IEEE Technical Applications Conference and Workshops. Northcon/*95, Portland, OR, 1995, pp. 116-119.

[3] F. Di Francesco, R. Fuoco, M. G. Trivella, and A. Ceccarini, "Breath analysis: trends in techniques and clinical applications," *Microchemical Journal, vol.* 79, pp. 405-410, January 2005.

[4] W. Miekisch, J. K. Schubert, and G. F. E. Noeldge-Schomburg, "Diagnostic potential of breath analysis—focus on volatile organic compounds," *Clinica Chimica Acta*, vol. 347, pp. 25-39, September 2004.

[5] R. F. Machado, D. Laskowski, O. Deffenderfer, T. Burch, S. Zheng, P. J. Mazzone, et al., "Detection of lung cancer by sensor array analyses of exhaled breath," *American Journal of Respiratory and Critical Care Medicine*, vol. 171, pp. 1286-1291, June 2005.

[6] V. Ruzsanyi, P. Mochalski, A. Schmid, H. Wiesenhofer, M. Klieber, H. Hinterhuber, et al., "Ion mobility spectrometry for detection of skin volatiles," *Journal of Chromatography B*, vol. 911, pp. 84-92, 2012.

[7] H. Handa, A. Usuba, S. Maddula, J. I. Baumbach, M. Mineshita, and T. Miyazawa, "Exhaled breath analysis for lung cancer detection using ion mobility spectrometry," *PloS one, vol.* 9, p. e114555, 2014.

[8] H. H. Hill and G. Simpson, "Capabilities and limitations of ion mobility spectrometry for field screening applications," *Field Analytical Chemistry & Technology*, vol. 1, pp. 119-134, 1997.

[9] A. D. Wilson and M. Baietto, "Advances in electronic-nose technologies developed for biomedical applications," *Sensors*, vol. 11, pp. 1105-1176, 2011.

[10] A. De Vincentis, G. Pennazza, M. Santonico, U. Vespasiani-Gentilucci, G. Galati, P. Gallo, et al., "Breath-print analysis by e-nose for classifying and monitoring chronic liver disease: a proof-of-concept study," *Scientific reports*, vol. 6, 2016.

[11] L. Dentoni, L. Capelli, S. Sironi, R. D. Rosso, S. Zanetti, and M. D. Torre, "Development of an electronic nose for environmental odour monitoring," *Sensors*, vol. 12, pp. 14363-14381, 2012.

[12] C. Di Natale, A. Macagnano, F. Davide, A. D'Amico, R. Paolesse, T. Boschi, et al., "An electronic nose for food analysis," *Sensors and Actuators B: Chemical*, vol. 44, pp. 521-526, 1997.

[13] A. Berna, "Metal oxide sensors for electronic noses and their application to food analysis," *Sensors*, vol. 10, pp. 3882-3910, 2010.

[14] J. W. Grate, "Acoustic wave microsensor arrays for vapor sensing," *Chemical Reviews*, vol. 100, pp. 2627-2648, 2000.

[15] K. S. Suslick, N. A. Rakow, and A. Sen, "Colorimetric sensor arrays for molecular recognition," *Tetrahedron*, vol. 60, pp. 11133-11138, 2004.

[16] W. I. S. Galpothdeniy, K. S. McCarter, S. L. De Rooy, B. P. Regmi, S. Das, F. Hasan, et al., "Ionic liquid-based optoelectronic sensor arrays for chemical detection," *Rsc Advances*, vol. 4, pp. 7225-7234, 2014.

[17] F. Röck, N. Barsan, and U. Weimar, "Electronic nose: current status and future trends," *Chemical reviews*, vol. 108, pp. 705-725, 2008.

[18] H. Yu, X. Dai, G. Yao, and Z. Xiao, "Application of Gas Chromatography-Based Electronic Nose for Classification of Chinese Rice Wine by Wine Age," *Food analytical methods*, vol. 7, pp. 1489-1497, 2014.

[19] M. Śliwińska, P. Wiśniewska, T. Dymerski, W. Wardencki, and J. Namieśnik, "Application of Electronic Nose Based on Fast GC for Authenticity Assessment of Polish Homemade Liqueurs Called Nalewka," *Food Analytical Methods, pp.* 1-12, 2016.

[20] Z. Xiao, D. Yu, Y. Niu, F. Chen, S. Song, J. Zhu, et al., "Characterization of aroma compounds of Chinese famous liquors by gas chromatography-mass spectrometry and flash GC electronic-nose," *Journal of Chromatography B, vol.* 945, pp. 92-100, 2014.

[21] A. O. Antoce and I. Namolosanu, "Rapid and precise discrimination of wines by means of an electronic nose based on gas-chromatography," *Rev. Chim*, vol. 62, pp. 593-595, 2011.

[22] B. A. Suslick, L. Feng, and K. S. Suslick, "Discrimination of complex mixtures by a colorimetric sensor array: coffee aromas," *Analytical chemistry*, vol. 82, pp. 2067-2073, 2010.

[23] R. L. Grob and E. F. Barry, *Modern Practice of Gas Chromatography,* 4th ed. Hoboken, N.J.: Wiley-Interscience, 2004.

[24] R. Ghijsen, H. Poppe, J. Kraak, and P. Duysters, "The Mass Loadability of Various Stationary Phases in Gas Chromatography," *Chromatographia*, vol. 27, pp. 60-66, January 1989.

[25] B. C. Kaanta, H. Chen, and X. Zhang, "A monolithically fabricated gas chromatography separation column with an integrated high sensitivity thermal conductivity detector," *Journal of Micromechanics and Microengineering*, vol. 20, p. 055016, 2010.

[26] G. E. Spangler, "Height equivalent to a theoretical plate theory for rectangular GC columns," *Analytical Chemistry*, vol. 70, pp. 4805-4816, 1998.

[27] M. A. Zareian-Jahromi, M. Ashraf-Khorassani, L. T. Taylor, and M. Agah, "Design, Modeling, and Fabrication of MEMS-Based Multicapillary Gas Chromatographic Columns," *Microelectromechanical Systems, Journal of*, vol. 18, pp. 28-37, 2009.

[28] M. A. Zareian-Jahromi and M. Agah, "Microfabricated Gas Chromatography Columns With Monolayer-Protected Gold Stationary Phases," *Journal of Microelectromechanical Systems*, vol. 19, pp. 294-304, April 2010.

[29] T. Nakai, S. Nishiyama, M. Shuzo, J.-J. Delaunay, and I. Yamada, "Micro-fabricated semi-packed column for gas chromatography by using functionalized parylene as a stationary phase," *Journal of Micromechanics and Microengineering*, vol. 19, p. 065032, 2009.

[30] S. Ali, M. Ashraf-Khorassani, L. T. Taylor, and M. Agah, "MEMS-based semi-packed gas chromatography columns," *Sensors and Actuators B: Chemical*, vol. 141, pp. 309-315, Aug. 18, 2009.

[31] J. Sun, D. Cui, X. Chen, L. Zhang, H. Cai, and H. Li, "Fabrication and characterization of microelectromechanical systems-based gas chromatography column with embedded micro-posts for separation of environmental carcinogens," *Journal of Chromatography A*, vol. 1291, pp. 122-128, 2013.

[32] H. Shakeel and M. Agah, "Self-Patterned Gold-Electroplated Multicapillary Gas Separation Columns With MPG Stationary Phases," *Journal of Microelectromechanical Systems*, vol. 22, pp. 62-70, February 2013.

[33] B. Alfeeli, S. Narayanan, D. Moodie, P. Zellner, M. McMillan, D. Hirtenstein, et al., "Interchannel Mixing Minimization in Semi-Packed Micro Gas Chromatography Columns," *Sensors Journal, IEEE*, vol. 13, pp. 4312-4319, 2013.

[34] J. Sun, D. Cui, F. Guan, X. Chen, and L. Zhang, "High resolution microfabricated gas chromatography column with porous silicon acting as support," *Sensors and Actuators B: Chemical*, vol. 201, pp. 19-24, 2014.

[35] R. Haudebourg, J. Vial, D. Thiebaut, K. Danaie, J. Breviere, P. Sassiat, et al., "Temperature-Programmed Sputtered Micromachined Gas Chromatography Columns: An Approach to Fast Separations in Oilfield Applications," *Analytical Chemistry*, vol. 85, pp. 114-120, 2012.

[36] J. Vial, D. Thiébaut, F. Marty, P. Guibal, R. Haudebourg, K. Nachef, et al., "Silica sputtering as a novel collective stationary phase deposition for microelectromechanical system gas chromatography column: Feasibility and first separations," *Journal of Chromatography A*, vol. 1218, pp. 3262-3266, 2011.

[37] H. Shakeel and M. Agah, in *Analytical Separation Science Sub- and Supercritical Chromatography*. vol. 3, Jared I. Anderson and V. Pino, Eds., ed: Wiley-VCH 2015.

[38] M. Stadermann, A. D. McBrady, B. Dick, V. R. Reid, A. Noy, R. E. Synovec, et al., "Ultrafast gas chromatography on single-wall carbon nanotube stationary phases in microfabricated channels," *Analytical Chemistry*, vol. 78, pp. 5639-5644, Aug. 15, 2006.

[39] B. Alfeeli, S. Narayanan, D. Moodie, P. Zellner, M. McMillan, D. Hirtenstein, et al., "Interchannel Mixing Minimization in Semi-packed Micro Gas Chromatography Columns," *IEEE Sensors Journal*, vol. PP, pp. 1-1, 2013.

[40] H. Shakeel, D. Wang, J. R. Heflin, and M. Agah, "Improved self-assembled thiol stationary phases in microfluidic gas separation columns," *Sensors and Actuators B-Chemical*, vol. 216, pp. 349-357, September 2015.

[41] H. Shakeel and M. Agah, "High-Performance Multicapillary Gas Separation Columns with MPG Stationary Phases," 2011 *Ieee Sensors*, pp. 1909-1912, 2011.

[42] D. Wang, H. Shakeel, J. Lovette, G. W. Rice, J. R. Heflin, and M. Agah, "Highly Stable Surface Functionalization of Microgas Chromatography Columns Using Layer-by-Layer Self-Assembly of Silica Nanoparticles," *Analytical Chemistry*, vol. 85, pp. 8135-8141, Sep. 3, 2013.

[43] H. Shakeel, D. Wang, R. Heflin, and M. Agah, "Width-modulated microgas chromatography separation columns with silica nanoparticles stationary phase," 2013 *Ieee Sensors*, pp. 8-11, 2013.

[44] D. Wang, A. Muhammad, J. R. Heflin, and M. Agah, "Novel Layer-by-Layer Silica Nanoparticles as an adorbent bed for Micro-fabricated Preconcentrators," 2012 *Ieee Sensors Proceedings*, pp. 119-122, 2012.

[45] B. Alfeeli, S. Ali, V. Jain, R. Montazami, J. Heflin, and M. Agah, "MEMS-based gas chromatography columns with nano-structured stationary phases," in *Sensors,* 2008 *IEEE,* 2008, pp. 728-731.

[46] M. D. Joshi and J. L. Anderson, "Recent advances of ionic liquids in separation science and mass spectrometry," *Rsc Advances*, vol. 2, pp. 5470-5484, 2012.

[47] C. F. Poole and S. K. Poole, "Ionic liquid stationary phases for gas chromatography," *Journal of separation science*, vol. 34, pp. 888-900, 2011.

[48] J. L. Anderson and D. W. Armstrong, "Immobilized ionic liquids as high-selectivity/high-temperature/high-stability gas chromatography stationary phases," *Analytical chemistry*, vol. 77, pp. 6453-6462, 2005.

[49] D. W. Armstrong, L. He, and Y.-S. Liu, "Examination of ionic liquids and their interaction with molecules, when used as stationary phases in gas chromatography," *Analytical chemistry*, vol. 71, pp. 3873-3876, 1999.

[50] J. Ding, T. Welton, and D. W. Armstrong, "Chiral ionic liquids as stationary phases in gas chromatography," *Analytical chemistry*, vol. 76, pp. 6819-6822, 2004.

[51] C. Ragonese, D. Sciarrone, P. Q. Tranchida, P. Dugo, and L. Mondello, "Use of ionic liquids as stationary phases in hyphenated gas chromatography techniques," *Journal of Chromatography A*, vol. 1255, pp. 130-144, 2012.

[52] W. I. S. Galpothdeniya, K. S. McCarter, S. L. De Rooy, B. P. Regmi, S. Das, F. Hasan, et al., "Ionic liquid-based optoelectronic sensor arrays for chemical detection," *RSC Advances*, vol. 4, pp. 7225-7234, 2014.

[53] B. P. Regmi, N. C. Speller, M. J. Anderson, J. O. Brutus, Y. Merid, S. Das, et al., "Molecular weight sensing properties of ionic liquid-polymer composite films: theory and experiment," *Journal of Materials Chemistry C*, vol. 2, pp. 4867-4878, 2014.

[54] N. C. Speller, N. Siraj, B. P. Regmi, H. Marzoughi, C. Neal, and I. M. Warner, "Rational design of QCM-D virtual sensor arrays based on film thickness, viscoelasticity, and harmonics for vapor discrimination," *Analytical chemistry*, vol. 87, pp. 5156-5166, 2015.

[55] A. Rehman and X. Zeng, "Methods and approaches of utilizing ionic liquids as gas sensing materials," *Rsc Advances*, vol. 5, pp. 58371-58392, 2015.

[56] X. Shi, L. Qiao, and G. Xu, "Recent development of ionic liquid stationary phases for liquid chromatography," *Journal of Chromatography A*, vol. 1420, pp. 1-15, 2015.

[57] P. Berton, B. P. Regmi, D. A. Spivak, and I. M. Warner, "Ionic liquid-based dispersive microextraction of nitrotoluenes in water samples," *Microchimica Acta*, vol. 181, pp. 1191-1198, 2014.

[58] B. P. Regmi, J. Monk, B. El-Zahab, S. Das, F. R. Hung, D. J. Hayes, et al., "A novel composite film for detection and molecular weight determination of organic vapors," *Journal of Materials Chemistry*, vol. 22, pp. 13732-13741, 2012.

[59] W. I. S. Galpothdeniya, B. P. Regmi, K. S. McCarter, S. L. de Rooy, N. Siraj, and I. M. Warner, "Virtual Colorimetric Sensor Array: Single Ionic Liquid for Solvent Discrimination," *Analytical chemistry*, vol. 87, pp. 4464-4471, 2015.

[60] M. H. Abraham, "Scales of solute hydrogen-bonding: their construction and application to physicochemical and biochemical processes," *Chemical Society Reviews*, vol. 22, pp. 73-83, 1993.

[61] P. Twu, Q. Zhao, W. R. Pitner, W. E. Acree, G. A. Baker, and J. L. Anderson, "Evaluating the solvation properties of functionalized ionic liquids with varied cation/anion composition using the solvation parameter model," *Journal of Chromatography A*, vol. 1218, pp. 5311-5318, 2011.

[62] J. L. Anderson, J. Ding, T. Welton, and D. W. Armstrong, "Characterizing ionic liquids on the basis of multiple solvation interactions," *Journal of the American Chemical Society*, vol. 124, pp. 14247-14254, 2002.

[63] J. L. Anderson, D. W. Armstrong, and G.-T. Wei, "Ionic liquids in analytical chemistry," *Analytical Chemistry*, vol. 78, pp. 2892-2902, 2006.

[64] L. W. Hantao, A. Najafi, C. Zhang, F. Augusto, and J. L. Anderson, "Tuning the selectivity of ionic liquid stationary phases for enhanced separation of nonpolar analytes in kerosene using multidimensional gas chromatography," *Analytical chemistry*, vol. 86, pp. 3717-3721, 2014.

[65] Q. Q. Baltazar, S. K. Leininger, and J. L. Anderson, "Binary ionic liquid mixtures as gas chromatography stationary phases for improving the separation selectivity of alcohols and aromatic compounds," *Journal of Chromatography A*, vol. 1182, pp. 119-127, 2008.

[66] G. R. Lambertus, J. A. Crank, M. E. McGuigan, S. Kendler, D. W. Armstrong, and R. D. Sacks, "Rapid determination of complex mixtures by dual-column gas chromatography with a novel stationary phase combination and spectrometric detection," *Journal of Chromatography A*, vol. 1135, pp. 230-240, 2006.

[67] J. V. Seeley, S. K. Seeley, E. K. Libby, Z. S. Breitbach, and D. W. Armstrong, "Comprehensive two-dimensional gas chromatography using a high-temperature phosphonium ionic liquid column," *Analytical and bioanalytical chemistry*, vol. 390, pp. 323-332, 2008.

[68] M. Qi and D. W. Armstrong, "Dicationic ionic liquid stationary phase for GC-MS analysis of volatile compounds in herbal plants," *Analytical and bioanalytical chemistry*, vol. 388, pp. 889-899, 2007.

[69] J. L. Anderson, R. Ding, A. Ellern, and D. W. Armstrong, "Structure and properties of high stability geminal dicationic ionic liquids," *Journal of the American Chemical Society*, vol. 127, pp. 593-604, 2005.

[70] P. Wisniewska, M. Sliwinska, J. Namiesnik, W. Wardencki, and T. Dymerski, "The Verification of the Usefulness of Electronic Nose Based on Ultra-Fast Gas Chromatography and Four Different Chemometric Methods for Rapid Analysis of Spirit Beverages," *Journal of Analytical Methods in Chemistry,* 2016.

[71] S. Stewart, M. A. Ivy, and E. V. Anslyn, "The use of principal component analysis and discriminant analysis in differential sensing routines," *Chemical Society Reviews*, vol. 43, pp. 70-84, 2014.

[72] J. Yan, X. Z. Guo, S. K. Duan, P. F. Jia, L. D. Wang, C. Peng, et al., "Electronic Nose Feature Extraction Methods: A Review," *Sensors*, vol. 15, pp. 27804-27831, November 2015.

[73] L. X. Huang, H. R. Liu, B. Zhang, and D. Wu, "Application of Electronic Nose with Multivariate Analysis and Sensor Selection for Botanical Origin Identification and Quality Determination of Honey," *Food and Bioprocess Technology*, vol. 8, pp. 359-370, February 2015.

[74] M. Akbar, M. Restaino, and M. Agah, "Chip-scale gas chromatography: From injection through detection," *Microsystems & Nanoengineering*, vol. 1, p. 15039, 12/21/online 2015.

[75] S. Narayanan, B. Alfeeli, and M. Agah, "Two-Port Static Coated Micro Gas Chromatography Column With an Embedded Thermal Conductivity Detector," *Ieee Sensors Journal*, vol. 12, June 2012.

[76] H. Shakeel, D. Wang, J. R. Heflin, and M. Agah, "Width-Modulated Microfluidic Columns for Gas Separations," *Ieee Sensors Journal*, vol. 14, pp. 3352-3357, October 2014.

[77] Y. Yang, M. D. Ferro, I. Cavaco, and Y. Liang, "Detection and identification of extra virgin olive oil adulteration by GC-MS combined with chemometrics," *Journal of agricultural and food chemistry*, vol. 61, pp. 3693-3702, 2013.

[78] A. I. Ruiz-Matute, A. C. Soria, I. Martinez-Castro, and M. Sanz, "A new methodology based on GC-MS to detect honey adulteration with commercial syrups," *Journal of agricultural and food chemistry*, vol. 55, pp. 7264-7269, 2007.

[79] A. I. Ruiz-Matute, S. Rodriguez-Sanchez, M. Sanz, and I. Martinez-Castro, "Detection of adulterations of honey with high fructose syrups from inulin by GC analysis," *Journal of food composition and analysis*, vol. 23, pp. 273-276, 2010.

ASPECTS OF THE DISCLOSURE

The present disclosure will be better understood upon reading the following numbered aspects, which should not be confused with the claims. In some instance, the aspects below may be combined with one or more additional aspects or with other aspects described elsewhere in the disclosure and accompanying examples. All such variations and combinations are intended to be covered by the instant disclosure.

Aspect 1. A micro gas chromatographic device for rapid detection of volatile organic compounds in a sample comprising a plurality of volatile organic compounds, the device comprising:

a. a microfluidic separation column comprising a column inlet;

b. a plurality of capillaries, wherein each of the capillaries in the plurality of capillaries is independently in fluid communication with the microfluidic separation column at a capillary inlet, and wherein each of the capillaries in the plurality of capillaries has a capillary outlet opposite the capillary inlet;

c. a plurality of micro-detectors, wherein each of the micro-detectors in the plurality of micro-detectors is independently positioned at or near the outlet of a capillary in the plurality of capillaries and configured to detect one or more volatile organic compounds passing through the capillary.

Aspect 2. The micro gas chromatographic device according to any one of Aspects 1-11, wherein the plurality of capillaries comprises from 2 to 10 capillaries.

Aspect 3. The micro gas chromatographic device according to any one of Aspects 1-11, wherein each of the capillaries in the plurality of capillaries has a capillary length of about 50 cm to about 2.5 m.

Aspect 4. The micro gas chromatographic device according to any one of Aspects 1-11, wherein each of the capillaries in the plurality of capillaries has a width of about 50 μm to about 500 μm.

Aspect 5. The micro gas chromatographic device according to any one of Aspects 1-11, wherein one or more of the capillaries in the plurality of capillaries comprises an array of micro pillars.

Aspect 6. The micro gas chromatographic device according to any one of Aspects 1-11, wherein each array of micropillars has a geometry independently selected from the group consisting of semi-packed architectures, which can be staggered or unstaggered, in which the pillars have a pitch size of about 5 μm to about 50 μm and a row spacing of about 10 μm to about 100 μm.

Aspect 7. The micro gas chromatographic device according to any one of Aspects 1-11, wherein one or more of the capillaries in the plurality of capillaries comprise a stationary phase selected from the group consisting of polyunsaturated hydrocarbons such as squalene; petroleum based greases such as petrolatum hydrocarbon greases; polysiloxanes such as polydimethyl siloxane, phenylmethyl polysiloxane, trifluoropropylmethyl polysiloxane, and trifluoropropylmethyl polysiloxane; polyalkylene glycols such as polyethylene glycol and polypropylene glycol; gold nanoparticles; silica nanoparticles; alumina; ionic liquids such as 1-Butyl-3-methylimidazolium hexafluorophosphate, 1-Butyl-3-methylimidazolium bis(trifluoromethylsulfonyl)imide, trihexyltetradecyl-phosphonium bis(trifluoromethylsulfonyl)imide, 1-butylpyridinium bis(trifluoromethylsulfonyl)imide, trihexyl(tetradecyl)phosphonium bis[(trifluoromethyl)sulfonyl]imide, and trihexyl(tetradecyl)phosphonium chloride; metal organic frameworks; compounds having a structure according to the following formula

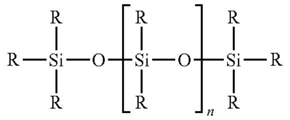

wherein n is an integer from 1 to 10 and each occurrence of R is independently selected from the group consisting of methyl, ethyl, phenyl, trifluoropropyl, —$C_3H_6CF$, cyanopropyl, and —$C_3H_6CN$; and stationary phases comprising a combination of the above.

Aspect 8. The micro gas chromatographic device according to any one of Aspects 1-11, wherein each of the micro-detectors in the plurality of micro-detectors is independently selected from the group consisting of a pTCD detector, a pFID detector, a MOS gas sensor, a capacitive detector, a MPN chemiresistor, a SAW detector, a pPID detector, a pPlasma ionization detector, and a combination thereof.

Aspect 9. The micro gas chromatographic device according to any one of Aspects 1-11, wherein each of the capillaries in the plurality of capillaries is distinct from each other in terms of one or more of a length, a width, a tortuosity, a presence or arrangement of an array of micro pillars, a surface functionalization, a type of detector at or near the outlet of the capillary, or a combination thereof.

Aspect 10. The micro gas chromatographic device according to any one of Aspects 1-11, further comprising a sample port in fluid commination with a micro-pump and in fluid communication with the column inlet; wherein the sample port, the micro-pump, and the column inlet are configured such that in a first setting the micro-pump draws a portion of the sample into the sample port and in a second setting injects the portion of the sample into the column inlet.

Aspect 11. The micro gas chromatographic device according to any one of Aspects 1-10, further comprising one or more on-chip heaters and one or more temperature sensors to control a temperature in one or more of the capillaries in the plurality of capillaries.

Aspect 12. A method of making a gas chromatographic device according to any one of Aspects 1-11, the method comprising:

a. applying a photoresist layer to a first surface of a silicon wafer to produce a mask layer;
b. patterning the mask layer using photolithography to produce a patterned mask layer defining at least the microfluidic separation column and plurality of capillaries; and
c. etching the silicon wafer having the patterned mask layer to produce an etched silicon wafer;
d. recleaning the etched silicon wafer; and
e. bonding a lid on the surface of the etched silicon wafer to form the microfluidic separation column and the plurality of capillaries.

Aspect 13. The method according to any one of Aspects 12-16, wherein the method comprises in step (c) timing the etching to control a depth of the microfluidic separation column and plurality of capillaries.

Aspect 14. The method according to any one of Aspects 12-16, wherein the silicon wafer comprises a silicon-on-insulator wafer comprising at least a wafer handle layer and a silicon oxide layer, and a. wherein the method comprises in step (c) etching the wafer handle layer until reaching the silicon oxide layer to control a depth of the microfluidic separation column and plurality of capillaries.

Aspect 15. The method according to any one of Aspects 12-16, wherein the method further comprises a step (a') prior to step (c), step (a') comprising bonding a glass or pyrex layer to a second surface of the silicon wafer opposite the first surface; and wherein the method comprises in step (c) etching the wafer to the glass or pyrex layer to control a depth of the microfluidic separation column and plurality of capillaries.

Aspect 16. The method according to any one of Aspects 12-16, wherein the method comprises functionalizing each of the capillaries in the plurality of capillaries with a different stationary phase by pumping each if the different stationary phases into a different outlet in the plurality of capillary outlets.

Aspect 17. A method of detecting one or more volatile organic compounds from a sample comprising a plurality of volatile organic compounds, the method comprising:

a. causing the sample to flow into the column inlet of a micro gas chromatographic device according to any one of Aspects 1-11, whereby each of the volatile organic compounds flows into one or more of the capillary inlets;
b. measuring a signal at one or more of the detectors in plurality of micro-detectors, wherein the one or more signals produced by the one or more detectors is indicative of a presence or an absence of a volatile organic compound in the plurality of volatile organic compounds.

Aspect 18. The method according to any one of Aspects 17-20, wherein the micro gas chromatographic device comprises a sample port in fluid commination with a micro-pump and in fluid communication with the column inlet;

i. wherein the method comprises placing the micro-pump in a first setting to draw a portion of the sample into the sample port; and
ii. wherein the method comprises placing the micro-pump in a second setting to inject the portion of the sample into the column inlet.

Aspect 19. The method according to any one of Aspects 17-20, further comprising controlling one or more of a flow rate of a carrier gas flowing into the column inlet, a temperature of a capillary in the plurality of capillaries, and a time period during which signals are detected at the one or more detectors.

Aspect 20. The method according to any one of Aspects 17-19, wherein the method comprises one or more of (i) a principal component analysis and (ii) a partial least squares regression over the signals from the one or more detectors for a period of time of about 30 second, about 10 second, about 5 seconds or less.

EXAMPLES

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

Example 1. Rapid Detection of Fuel Adulteration Using Microfabricated Gas Chromatography Rapid and accurate quality control for fuel adulteration is a major economic and health concern. Current technology lacks capability to provide speedy and accurate point of sale (POS) solutions. Most of the work done on portable solutions rely on absorbance spectroscopy, which provide a qualitative solution with a trade-off between speed and accuracy. This paper demonstrates a technique based on micro gas chromatography (μGC) for portable, fast, and accurate analysis of diesel fuels adulterated with kerosene. The separation columns are fabricated using microelectro-mechanical systems (MEMS) technology. The columns are 1 m-long and consist of an embedded array of pillars. Two different stationary phase coating were examined to explore the efficacy of the proposed technique. The analysis relies on aggressive pressure and temperature programming of the chip to obtain partially separated chromatograms. When analyzed with well-established chemometrics methods such as Principal Component Analysis and Partial least Squares Regression. a linear relationship between the chromatograms and diesel purity was determined. The separation column could discriminate as little as 5% added kerosene to diesel fuel with only four seconds of chromatogram analysis.

Materials and Methods

Column Design and Fabrication

Figure 5:
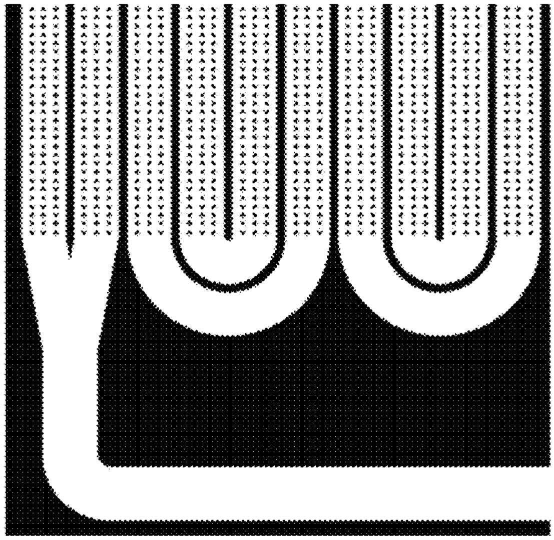
FIG. 5 is an exemplary mask layout segment for a separation column.
Figure 6:
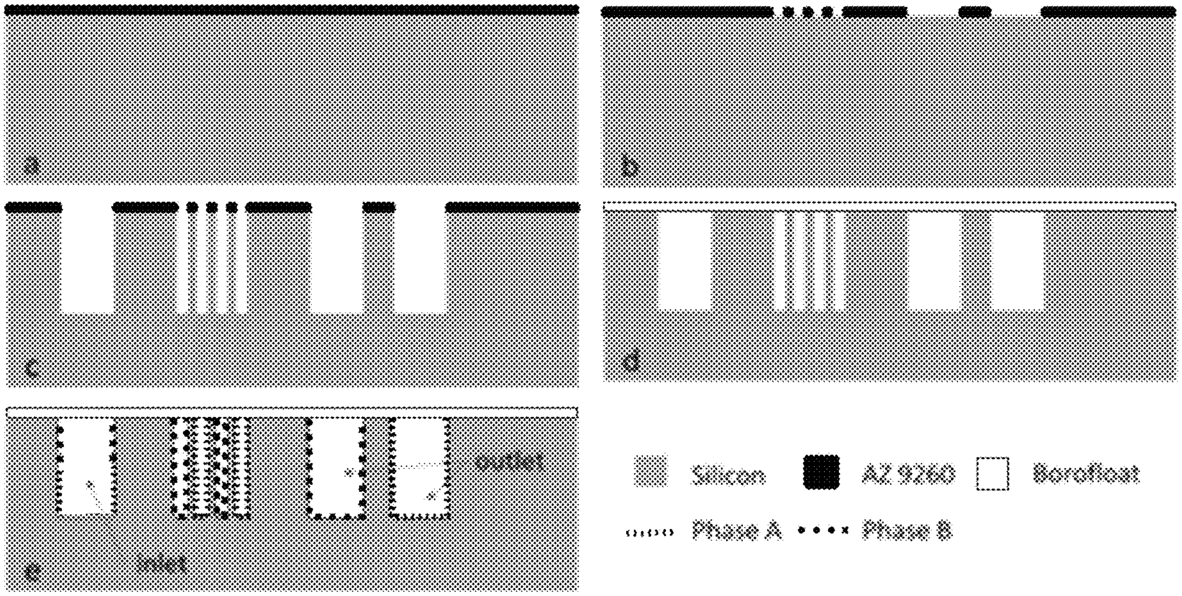
FIG. 6 depicts an exemplary process used to fabricate the multi-column micro gas chromatographic devices of the examples.
Figure 7:
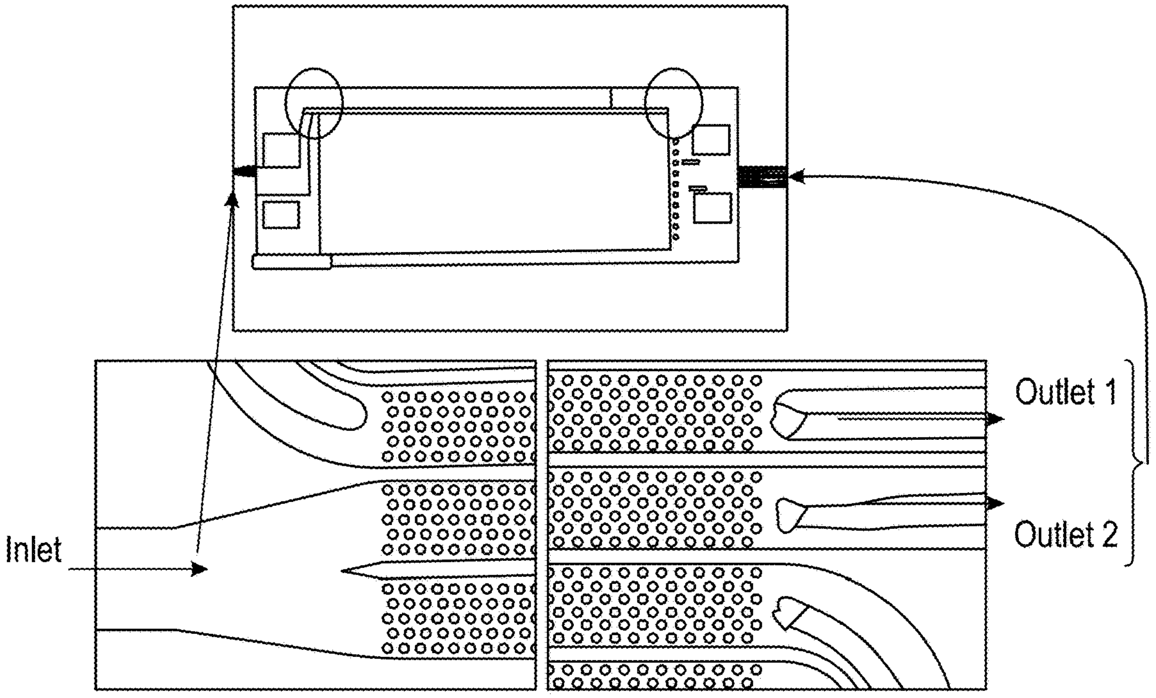
FIG. 7 is a set of imaged depicting the fabrication results showing micro separation column (top) and zoomed in pictures shows the inlet and outlets of the chip after coating (bottom).
Figure 8:
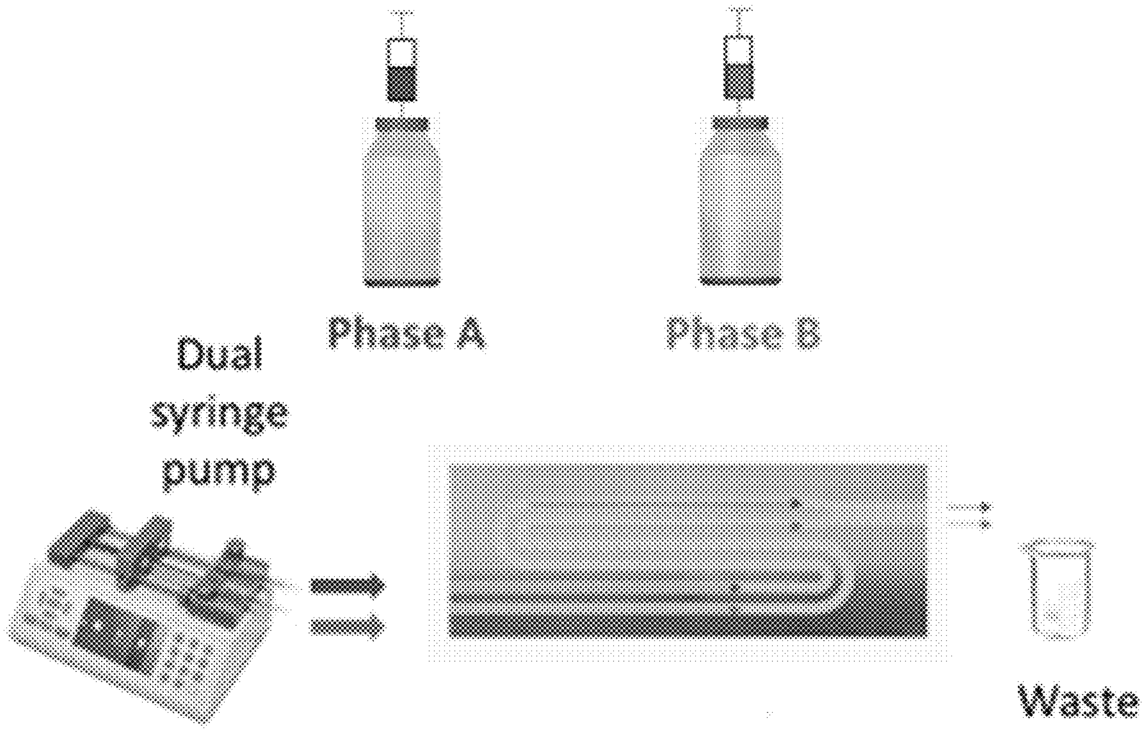
FIG. 8 is a schematic of the coating process where the two stationary phases are prepared in a solution of acetone, loaded in a syringe pump and injected at a rate of 20 μL through each outlet to coat both the columns simultaneously.

The design of the μGC chip follows our previously published semi-packed architecture [25]. Each channel includes 20 μm pillars with a pitch size of 20 μm in a row and 35 μm between each row. The overall length of each channel is 1 m, with the width set as 200 μm. The chip inlet bifurcates into two semi-packed channels each of which has its own outlet (FIGS. 5-6). Each column is coated with a different stationary phase enabling us to evaluate the effect of the phase on detecting adulteration in fuel samples. This was done to reduce chip to chip and wafer level variation among the two channels. The column mask design and fabrication process flow are illustrated in FIGS. 5-6. The fabrication result is shown in FIG. 7. The wafer is spun with photoresist (PR) AZ9260 @ 2000 rpm for 60 seconds after HMDS priming. The PR was soft baked for 2 minutes and 30 seconds at 110 C. The wafer was then rehydrated for 30 minutes. A PR thickness of 8.2 μm was achieved. The mask design is transferred on the wafer via lithography with MA-6 (Karl Suss) mask aligner. After development of the pattern with AZ400k (1:3 dilution, 3 minutes) the wafer was dried with nitrogen. Using deep reactive ion etching (DRIE) the design was etched to a channel depth of 250 μm. Plasma ashing was then performed to clean the wafer of left-over PR after acetone, IPA and DI water cleaning. Then the silicon wafer was bonded with a borofloat wafer using a Karl Suss, SB-6 anodic bonder. After dicing short fused silica capillary columns were connected to the device channels and sealed with epoxy. Two Room temperature Ionic Liquids (RTILs) were chosen as the stationary phases. While a further analysis with more traditional stationary phases would provide more insight into role of stationary phases, it would be a divergence from the investigation into micro GC's capability to detect fuel adulteration. This could a topic of interest for future research. We chose two different stationary phases with different polarities to investigated their effect on diesel purity identification. ([P66614][NTf2]) trihexyltetradecyl-phosphonium bis(trifluoromethylsulfonyl) imide is denoted as Phase A, and ([BPyr][NTf2]) 1-butylpyridinium bis(trifluoromethylsulfonyl)imide is named Phase B. The columns were coated using a modified static coating process. 15 mg of each phase was dissolved in 1 ml acetone. To coat the columns, we use a dual syringe pump. The coating process is illustrated in FIG. 8. We load the phases in syringes and connect them to the outlet of the device. We start injecting the phase solutions simultaneously through the outlets starting at 20 μL/min. After the columns are filled with the solution, we increase the rate to 40 μL/min. We further increase the injection rate to 60 μL/min with 100 μL remaining in the syringe to make sure to fill any residue uncoated parts. After the injection is completed, we connect the inlet of the device to an empty vial connected to a nitrogen cylinder. The device is submerged in a bath of water in a hotplate at 45° C. This evenly heats up the device while the nitrogen gas dries the acetone. The columns were conditioned with Thermofischer's Heratherm oven at 150° C.

Experimental Setup and Data Analysis

Diesel and kerosene were bought from "Briggs and Stratton" and "Crowne". They were mixed in volumetric ratios of 95/5 and 90/10% (v/v). Pure diesel was used as the control sample. All three different samples were kept refrigerated before, and after running the experiments, to keep their integrity intact. All testing was done with an Agilent 7890A GC which is equipped with an autoinjector and a flame ionization detector (FID). The fabricated columns were connected to the GC inlet. One of the outlets was connected to the FID. The inlet temperature was kept at 280° C. and the FID at 300° C. Ultra-high purity helium was chosen as the carrier gas. The tests were performed with a fast GC approach utilizing aggressive pressure and temperature programming. The run conditions were 80° C. initial temperature with 100° C./min temperature ramp with a final temperature of 150° C. (with 1 min hold time) run at 40 psi carrier gas pressure. The injection was performed in split mode at a split ratio of 200:1 with an injection volume of 0.3 μL. The data were obtained from Agilent ChemStation software. Each sample was run 11 times, with a total of 33 runs for all testing samples. Apart from the training samples, separate blind samples were taken for testing the trained models. The blind samples were prepared and put in unlabeled GC vials by a person who did not run the data analysis. The person performing the testing was not privy to the unlabeled samples values till after analysis was complete. This was done to prevent any observer bias in data analysis. We also ran 100% kerosene and 100% diesel samples at a 5° C./min temperature ramp with 30° C. initial temperature with a hold time of 0.5 minutes and 150° C. final temperature for both phases. This was done to illustrate the constituent differences in the fuels. Principal Component Analysis (PCA) and Partial Least Squares Regression (PLSR) were then performed on the chromatographic data. PCA is used for exploratory multivariate data analysis. The original data is reduced to a set of uncorrelated principal components that can show the differences between observations. PCA and PLSR are widely used tools in chemometrics for calibration [26, 27]. PCA is a dimensionality reduction technique. This is useful to visualize variations in higher dimensional data. PCA algorithm works by reducing original dataset of vectors and projects them onto a lower dimension vector while retaining the maximum variation possible from the original data set. PCA indicates that chromatographic patterns can be used to qualitatively discern adulterated and pure diesel. To quantitatively determine adulteration content, we use PLSR; a widely used technique for chemometric calibration. PLSR is an iterative algorithm that relates two groups of variables to each other, namely predictor (raw chromatograms) and response (concentration). Figures of merit (FOM) are indicators used to evaluate the accuracy and usefulness of the developed models. Root mean squared error gives an average distance of the calibration error from zero. Root mean squared error of cross validation (RMSECV) and root mean squared error of prediction (RMSEP)

are two metrics measured on the train and test set respectively. RMSECV gives a measure of how well the model can calibrate to training data. RMSEP gives the measure of model performance to unseen data [1].

Figures of Merit (FOM):

$$RMSE = \sqrt{\frac{1}{n}\sum_{i=1}^{n}({'y_i} - y_i)^2} \quad (1)$$

RMSE=Root mean square error

Where, 'y=predicted value and y=observed value $$R^2(y,'y) = 1 - \frac{\sum_{i=1}^{n}({'y_i} - y_i)^2}{\sum_{i=1}^{n}({''y_i} - y_i)^2} \quad (2)$$

$$\text{Where, } ''y = \frac{1}{n}\sum_{i=1}^{n} y_i$$

Results and Discussion

The choice of the stationary phase plays an important role in gas chromatography. Stationary phases exhibit varying selectivity depending on the type of analyte. Interactions between the analytes and the phases of similar polarities are highest. It increases the residence time in the stationary phase compared to analytes with a phase of opposing polarity. In our case, Phase B is more polar than Phase A [19]. The plate number of the columns were calculated with a solution of naphthalene in acetone with an isothermal run of 100° C. at different carrier gas pressures. The columns tested after conditioning showed an optimal operating pressure of around 20 psi. Phase A column had a plate number of 2117@ 20 psi while Phase B showed a plate number of 1126@ 25 psi.

Figure 12A:
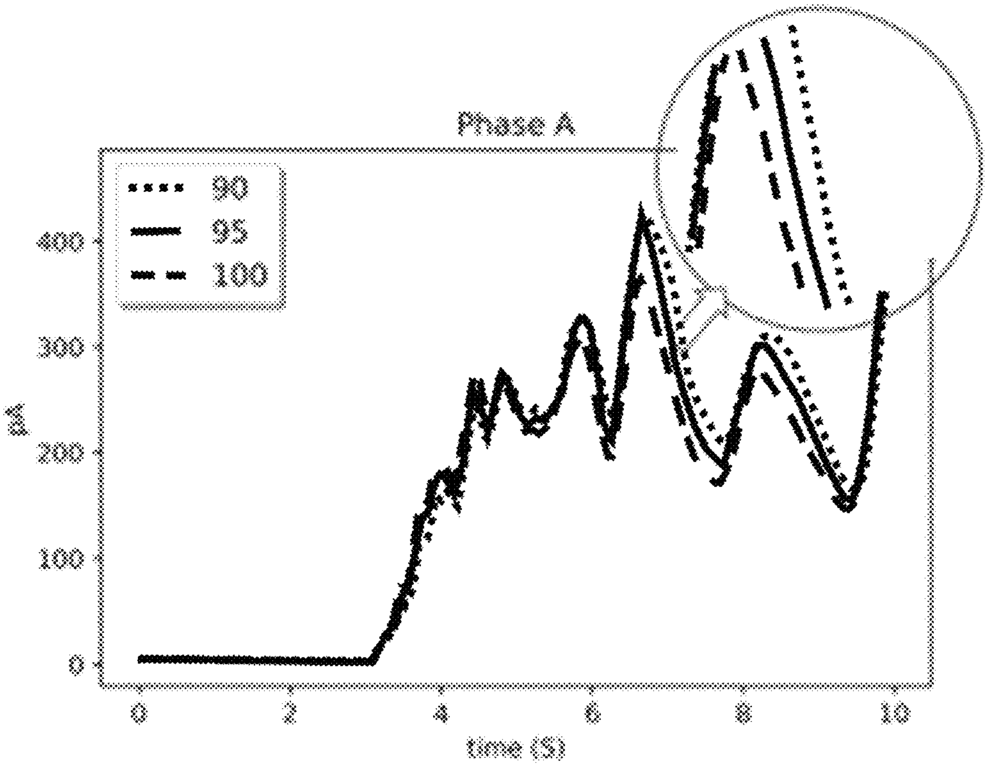
FIGS. 12A-12B are chromatogram overlay showing three different diesel concentrations of 90%, 95%, and 100% (v/v) in the first ten seconds for each of Phase A (FIG. 12A) and Phase B (FIG. 12B) respectively. Each concentration has 11 runs.
Figure 12B:
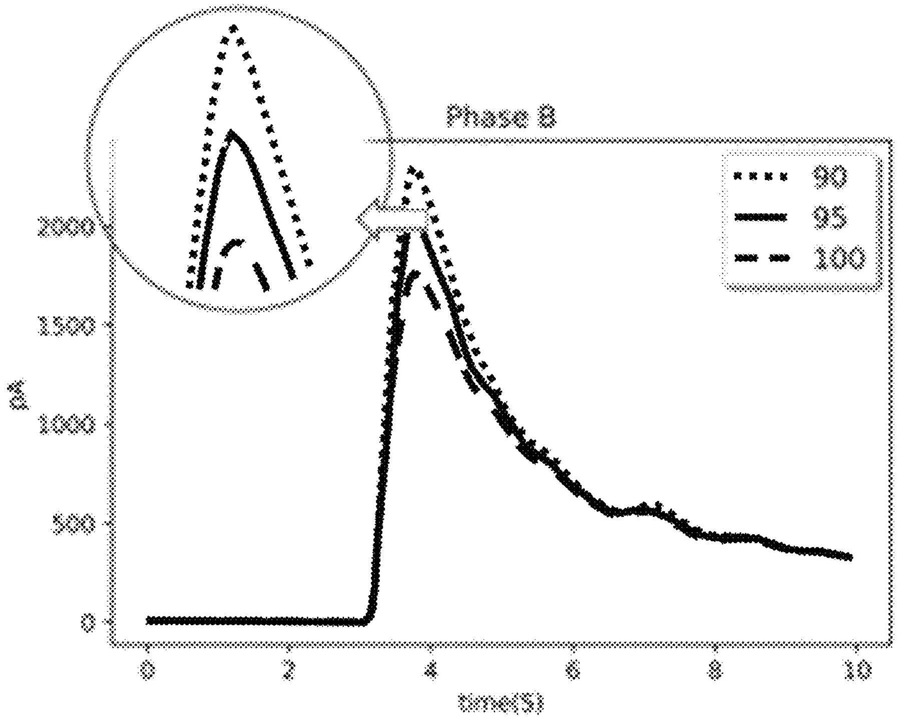
Figure 13A:
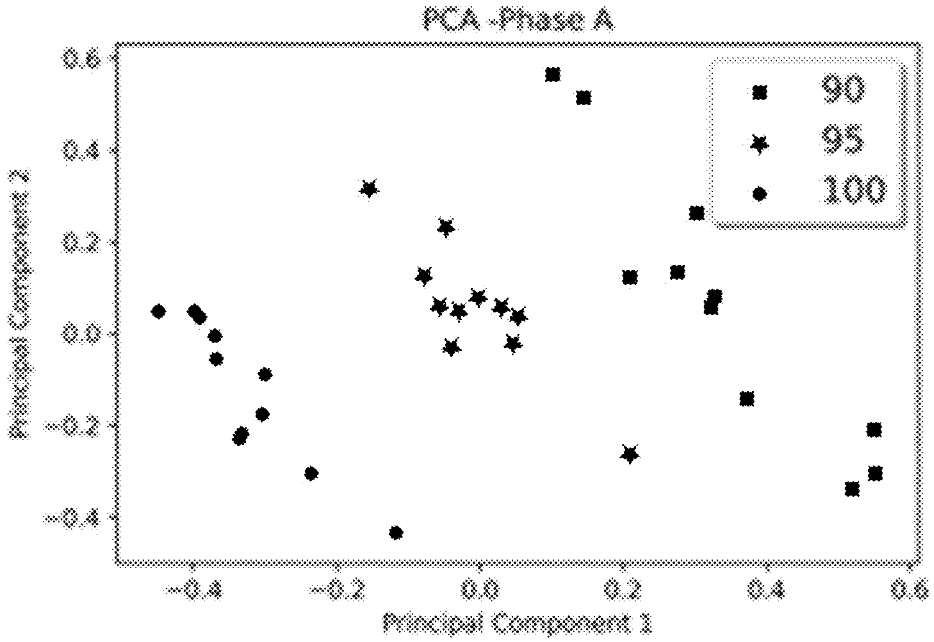
FIGS. 13A-13D depict PCA (FIGS. 13A-13B) and scree plots (FIGS. 13C-13D) for chromatograms from both Phase A (FIGS. 13A and 13C) and Phase B (FIGS. 13B and 13D). The PCA was performed on the full chromatogram obtained for both the phases. They show the chromatograms can be differentiated by PCA. The first two principal components account for ~90% of the variance explained in the data.
Figure 13B:
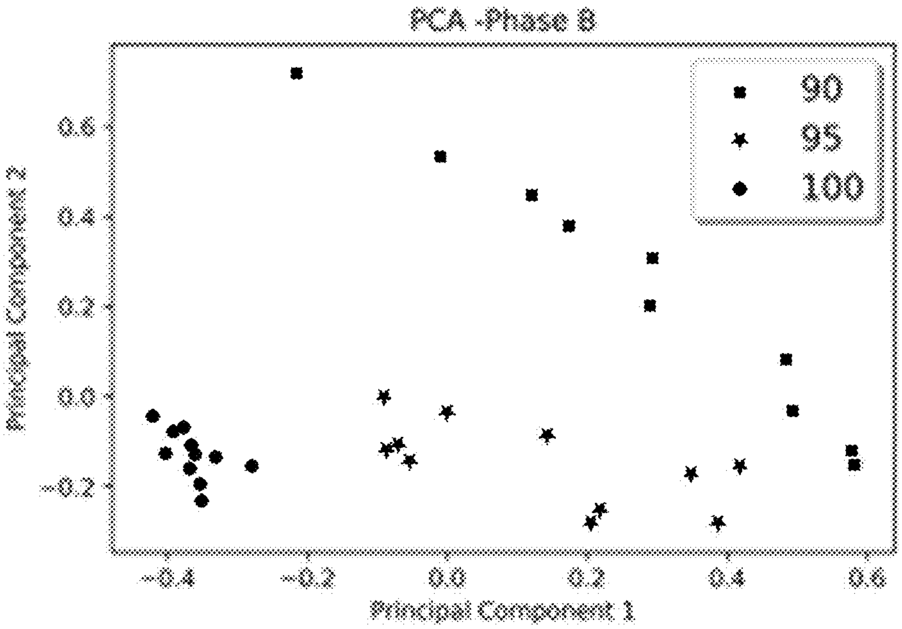
Figure 13C:
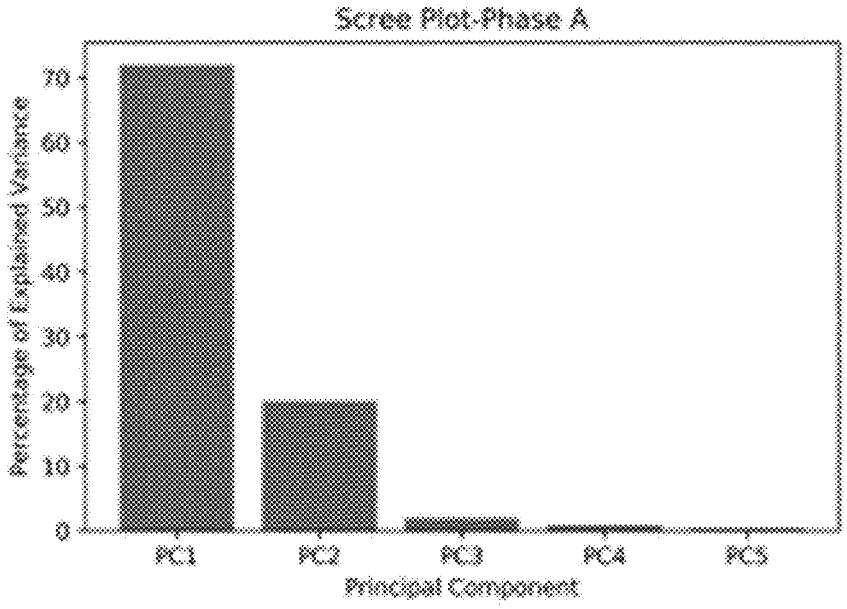
Figure 13D:
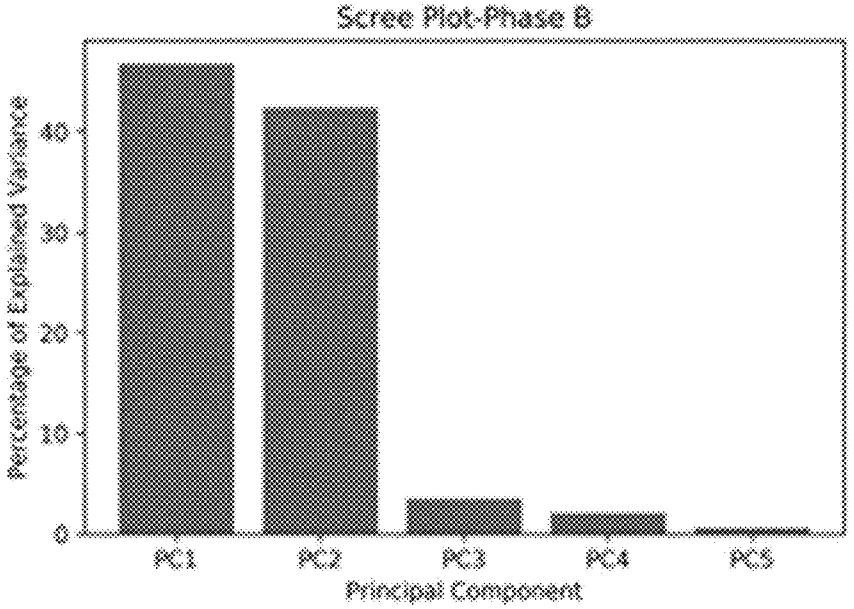

GC analysis usually relies on peak retention time index to identify chemicals in the sample. In this way, a fully resolved chromatogram can identify any compound in the mixture assuming there is no co-elution. For complex samples, slow temperature programming and longer columns are required to identify the majority of the compounds of interest. However, even these methods fail to separate very complex samples and novel techniques such as multi-dimensional GCs have to be used for comprehensive detection of all analytes. For portable systems this increase their size, weight and power consumption. In most applications, it is not required to have a completely resolved chromatogram since most of the information provided by the analysis is not required. A partially resolved chromatogram can provide enough information for the specific application. We investigated the chromatograms from the stand point of pattern recognition instead of the usual retention time index analysis. As stated previously, the GC was run in an aggressive temperature programming and pressure regime. It can be seen from the chromatogram (FIGS. 9A-9D, 10A-10D, and 11A-11D) that phase A does a decent job of separating the major hydrocarbons even in these conditions. Although it is incomplete, the separation can still be interpreted by a human observer. Phase B, however shows no appreciable separation whatsoever. It clearly cannot retain any of the low to mid boiling range analytes and releases them with a very short residence time in the stationary phase. This information is not useful for human interpretation by looking at retention time indexes. Diesel is primarily composed of non-polar alkanes with polar compounds accounting for less than 0.1% in mass [28]. These non-polar compounds and are not easily separated by Phase B (more polar) which would be an ineffective stationary phase to perform any reasonable separation of diesel or diesel-kerosene mixture. However, closer inspection of the data shows a trend among both phases for the purity of diesel (FIGS. 12A-12B).

Figure 14A:
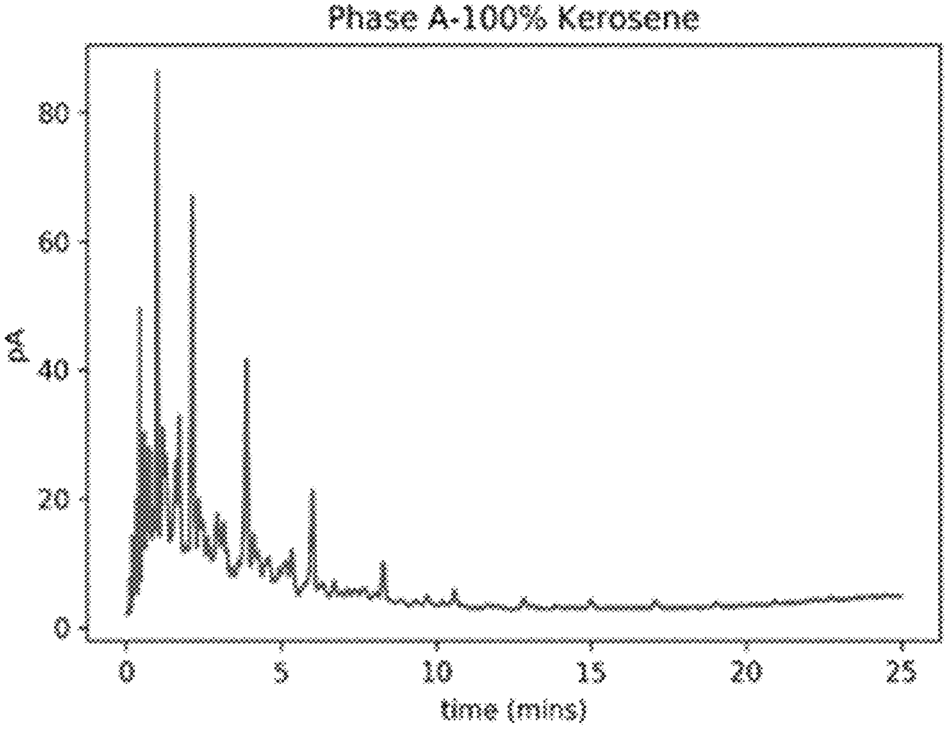
FIGS. 14A-14B are graphs of the chromatograms showing the difference in hydrocarbon content of diesel and kerosene with GC conditions at 5° C./min ramp rate from 30° C. to 150° C. @ 25 psi for 100% Kerosene (FIG. 14A) and 100% diesel (FIG. 14B).
Figure 14B:
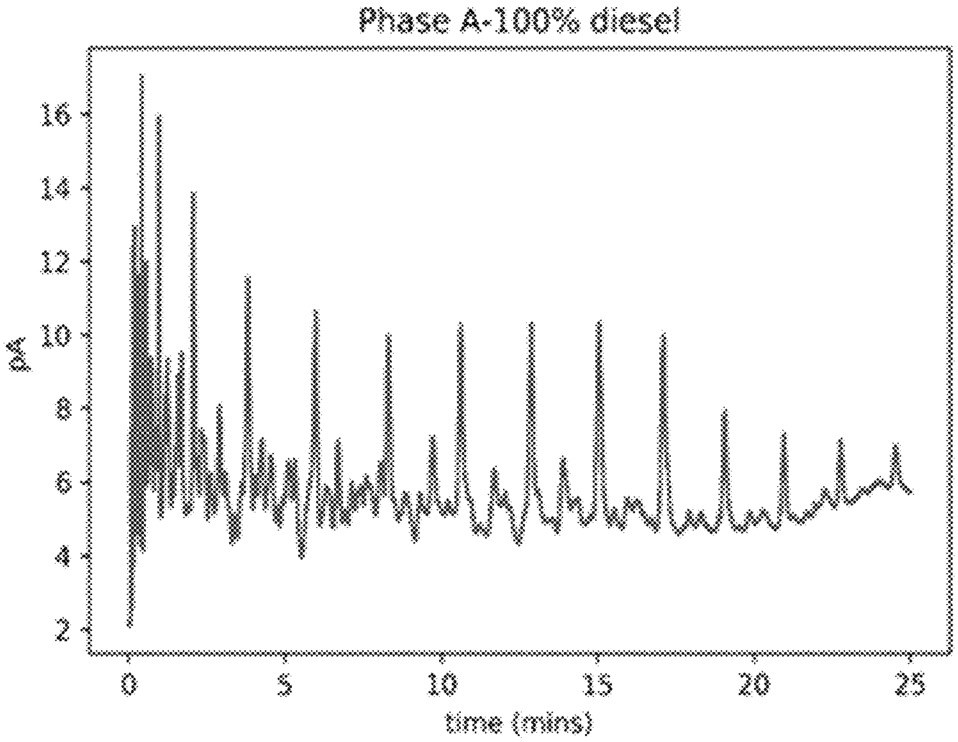

As mentioned above, PCA was used to determine if the chromatographic patterns contain sufficient information to discriminate between the samples. Before performing PCA, the data was preprocessed by scaling to unit variance after removing the mean. The data is then centered. The results of the PCA is shown in FIGS. 14A-14B. For both phases, the first two principal components (PC) explain approximately 90% of the variance explained in the data. The first two components can discriminate between diesel sample and altered ones. It also illustrates the run-to-run variation of the GC for the same concentrations. This can be attributed primarily to noise from GC instrumentation (gas flow control, temperature programming and data acquisition). The results show that PCA can be used to qualitatively judge the purity of fuel and give a decision on possible adulteration of diesel and warrant further investigation.

Figure 9A:
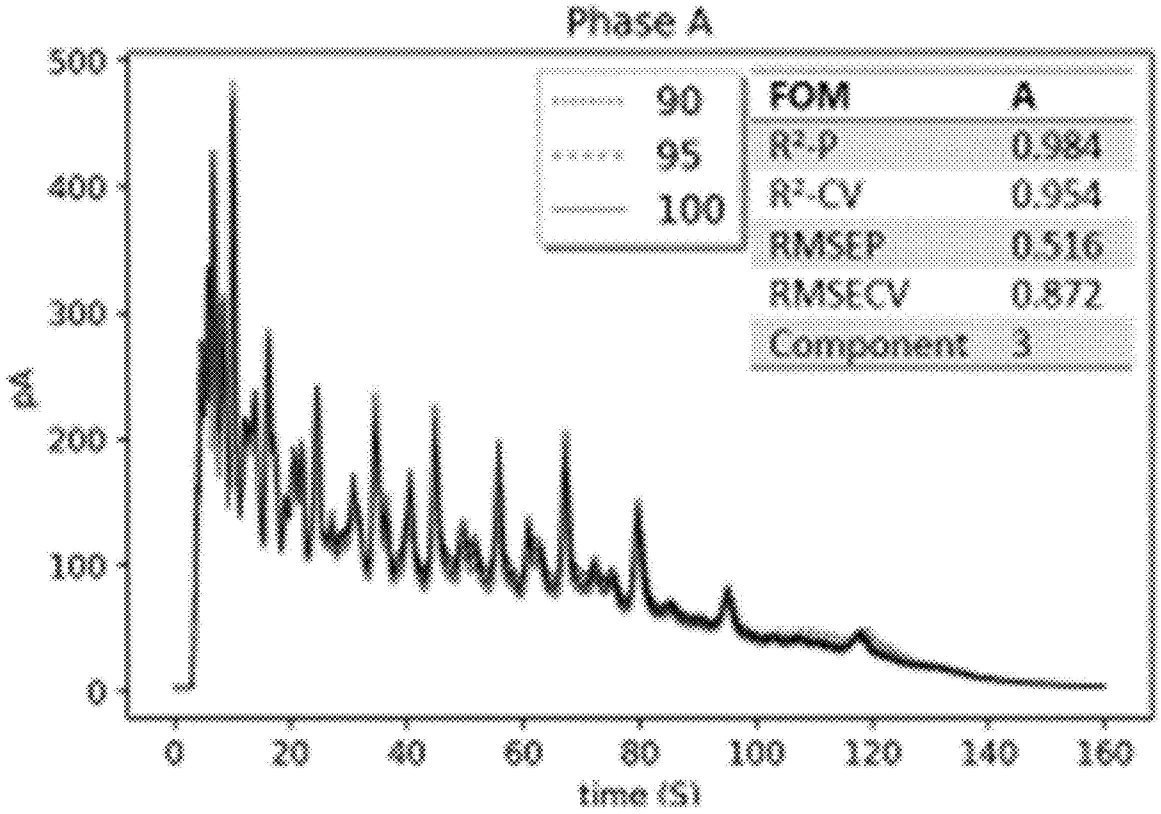
FIGS. 9A-9D demonstrate the data analysis for 160 s.
Figure 9B:
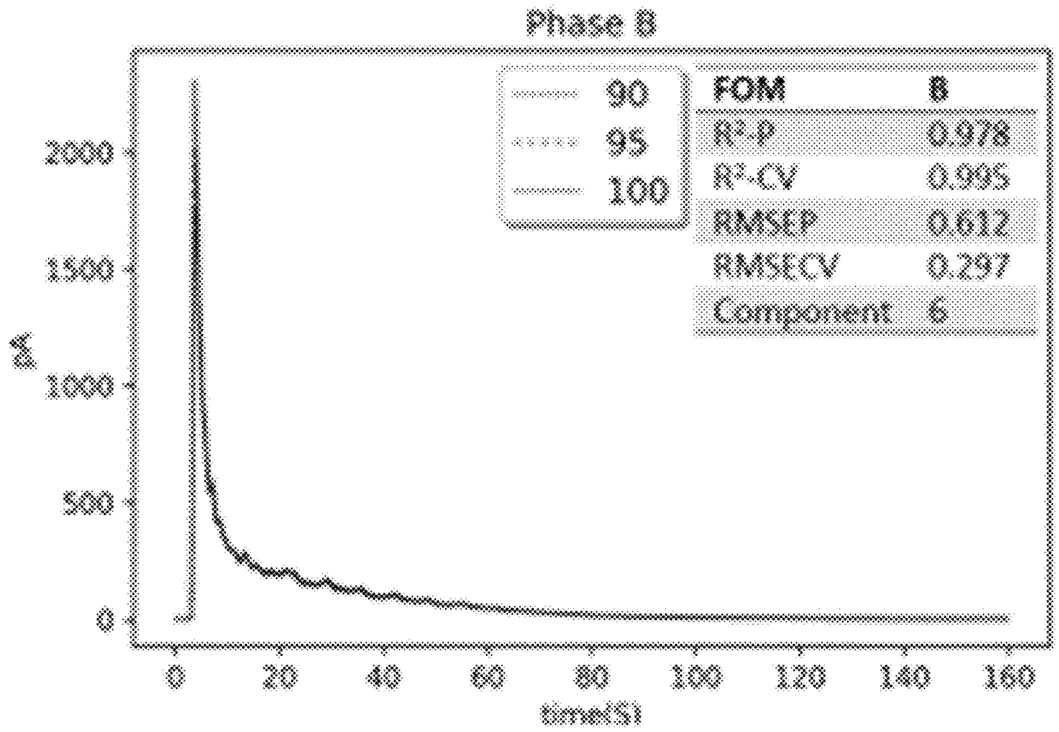
Figure 9C:
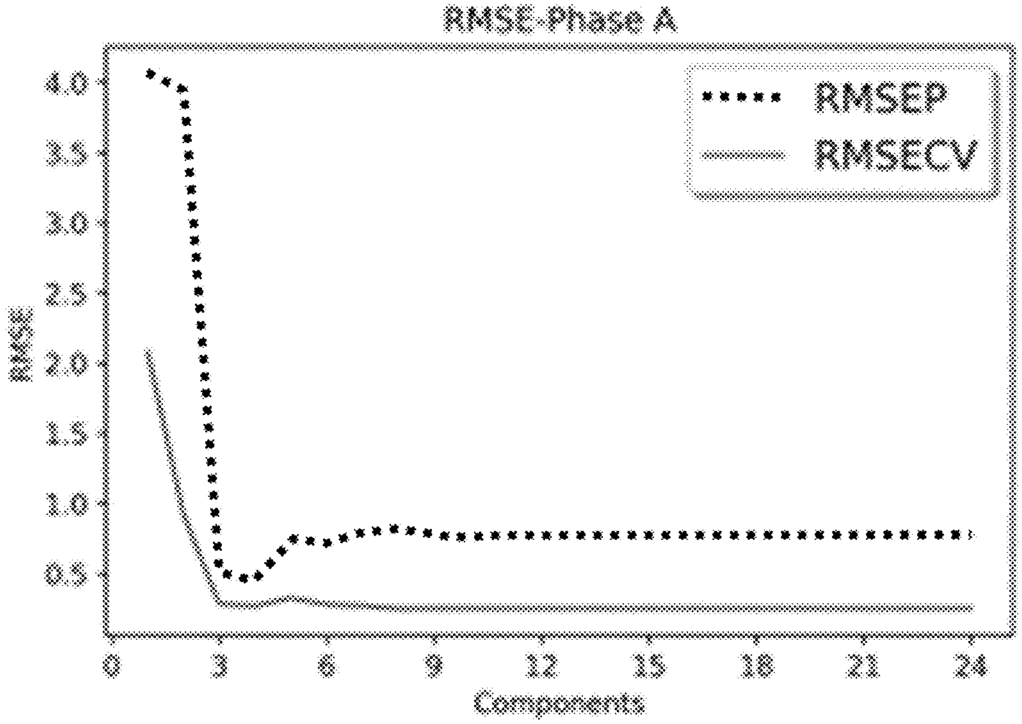
Figure 9D:
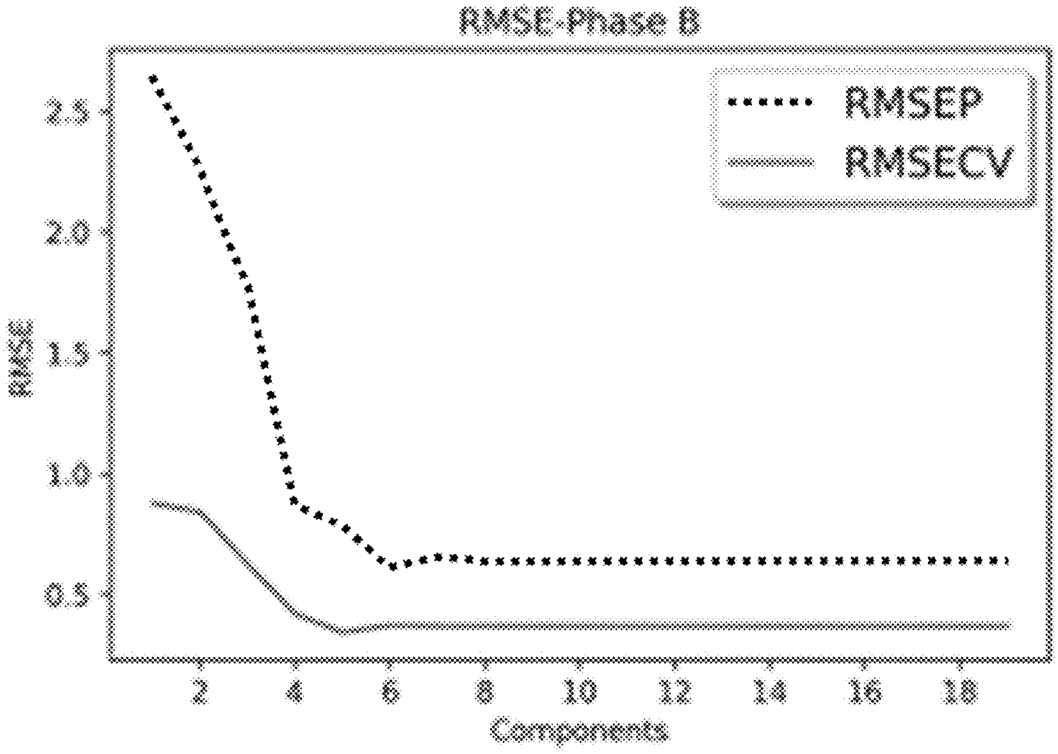
Figure 10A:
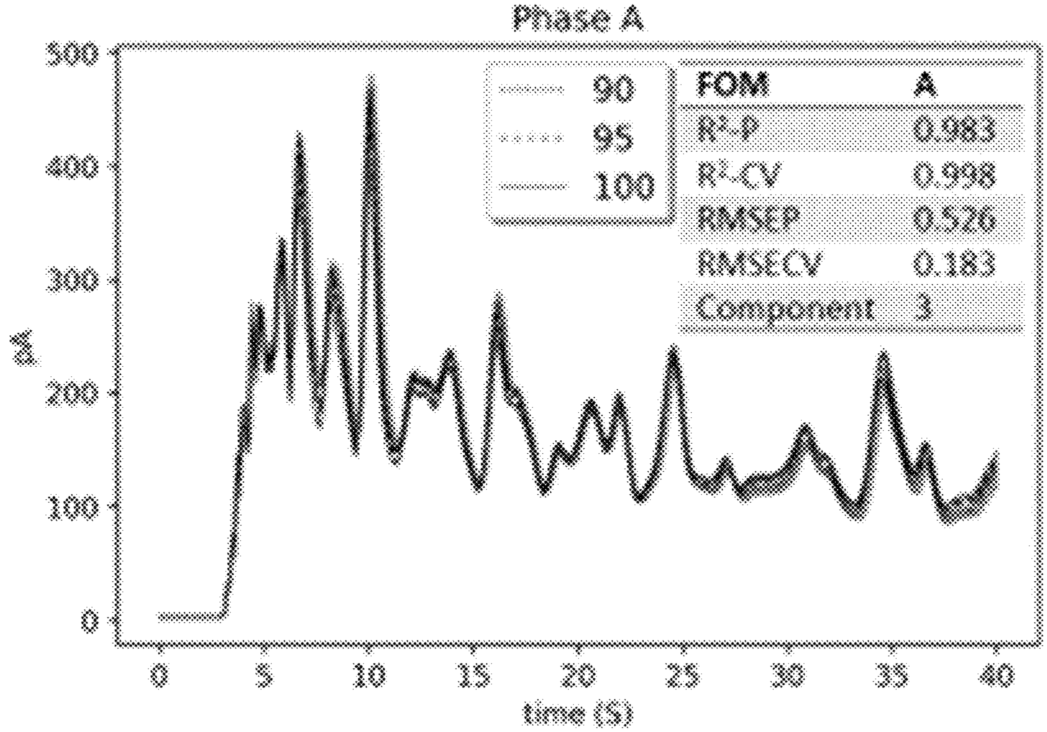
FIGS. 10A-10D demonstrate the data analysis for the first 40 s of the chromatorgram.
Figure 10B:
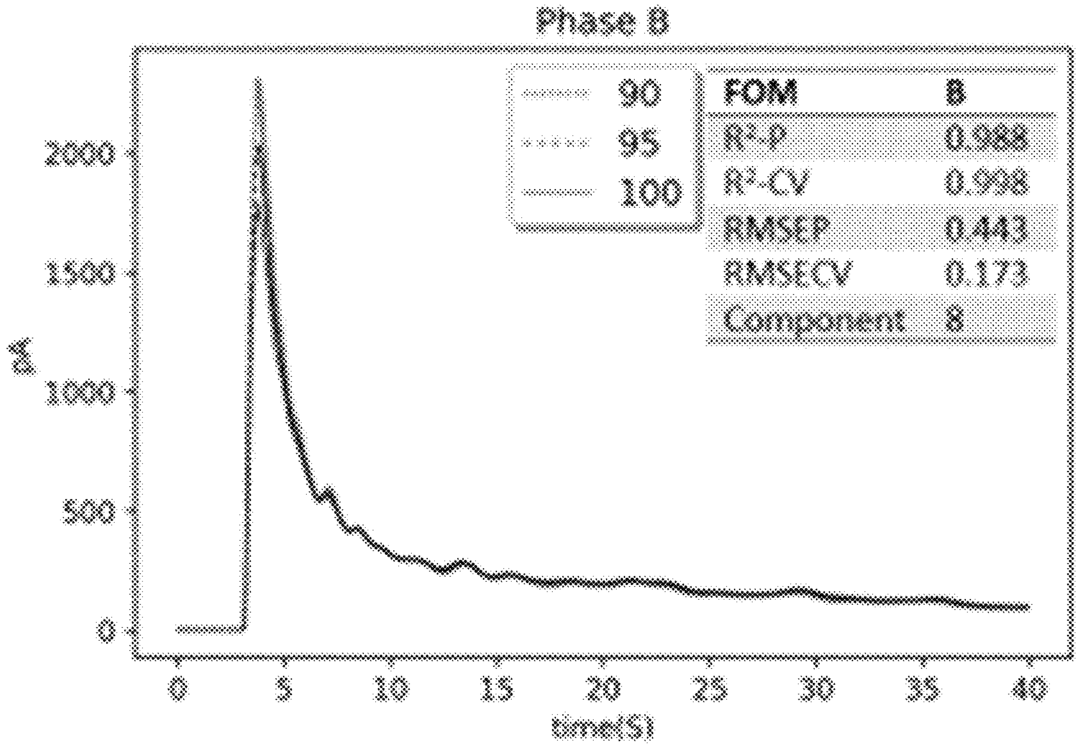
Figure 10C:
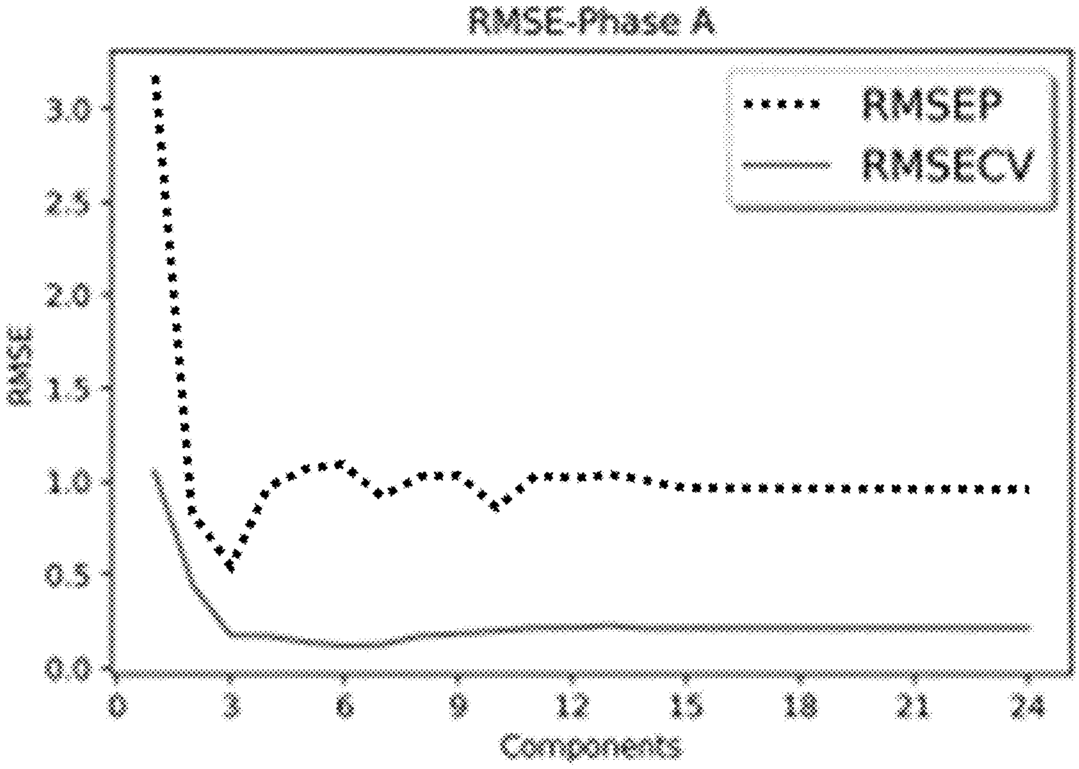
Figure 10D:
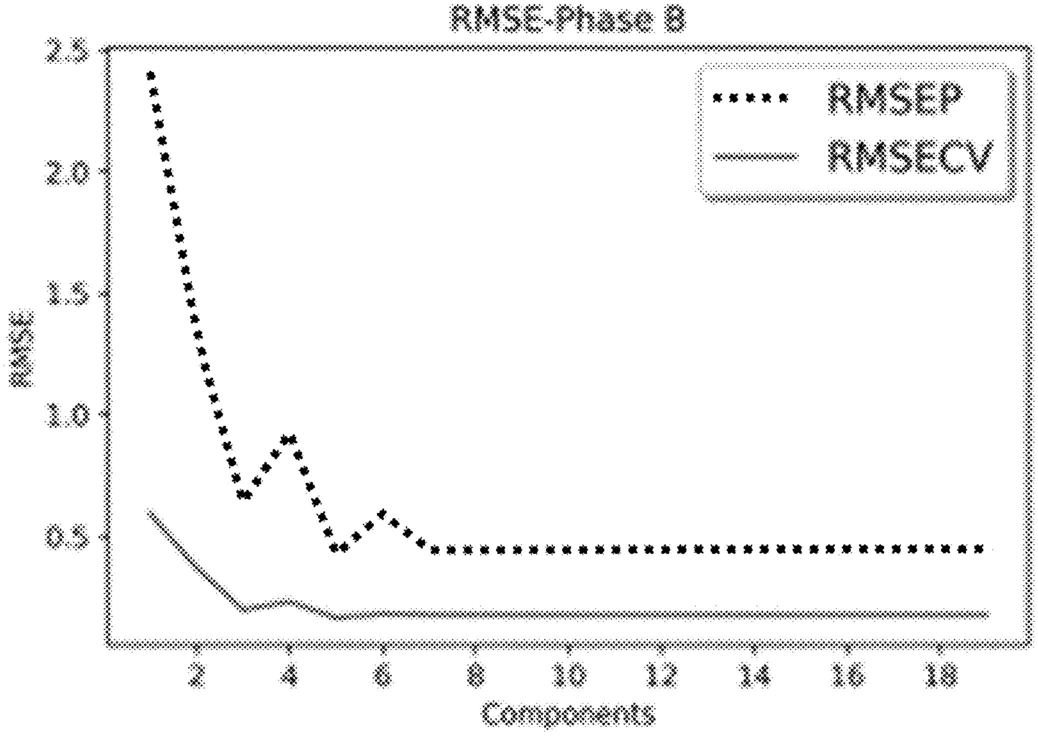
Figure 11A:
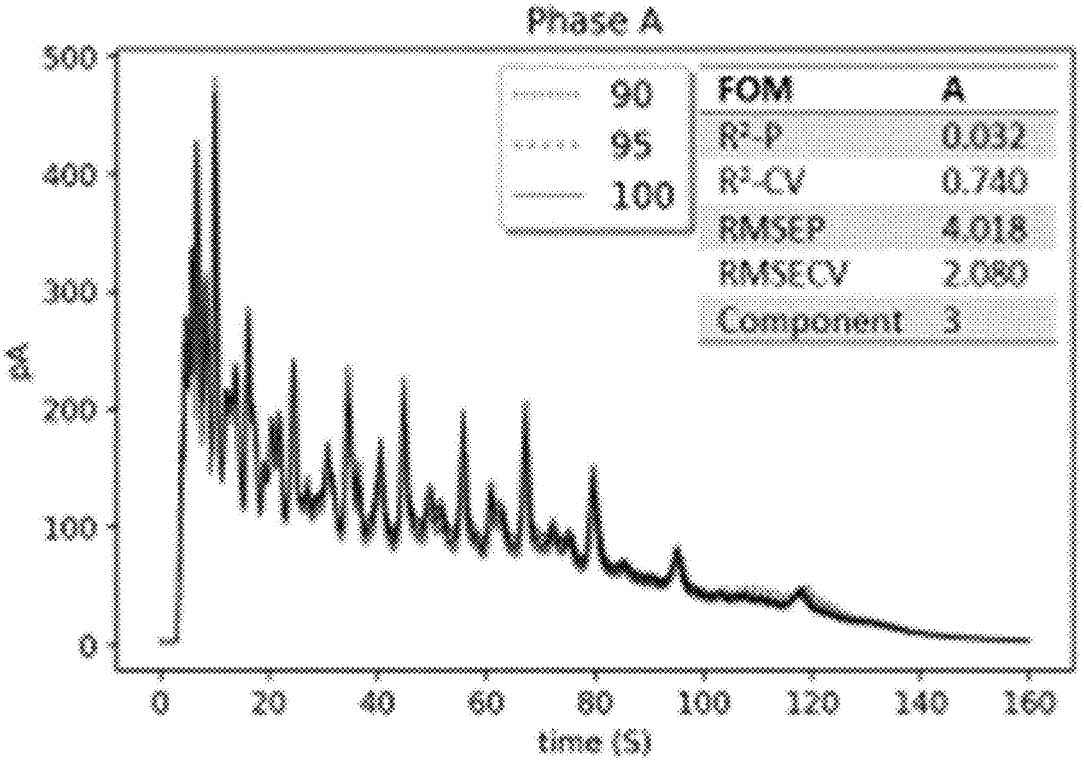
FIGS. 11A-11D demonstrate the data analysis for the first 4 s of the chromatorgram.
Figure 11B:
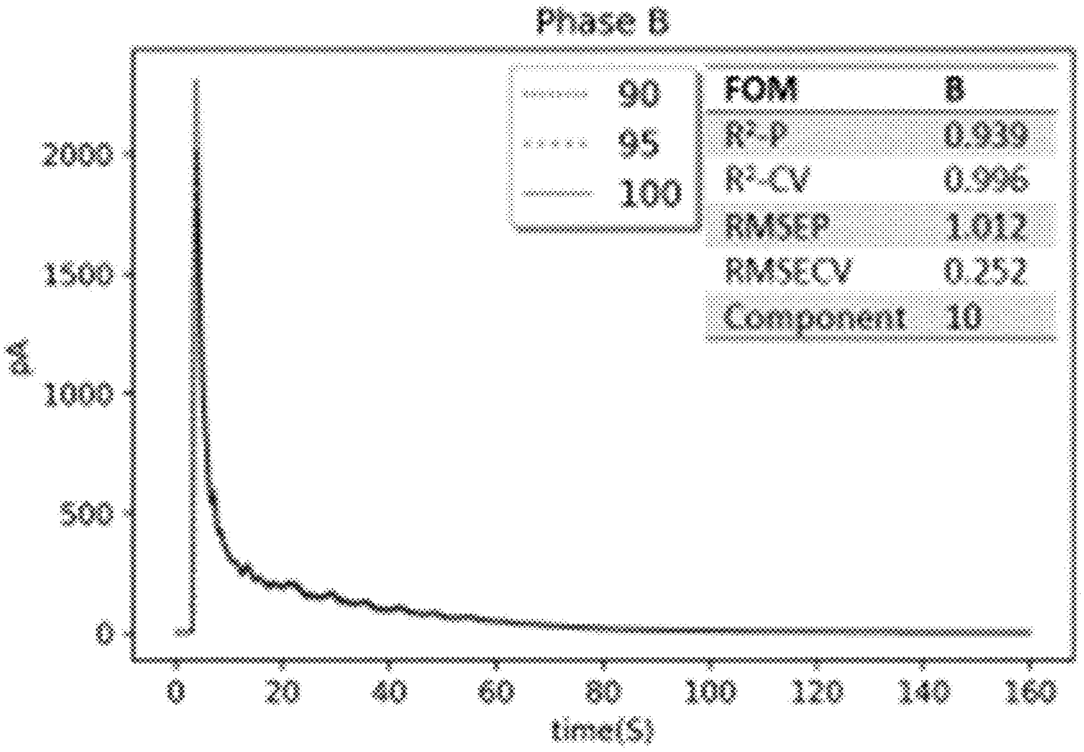
Figure 11C:
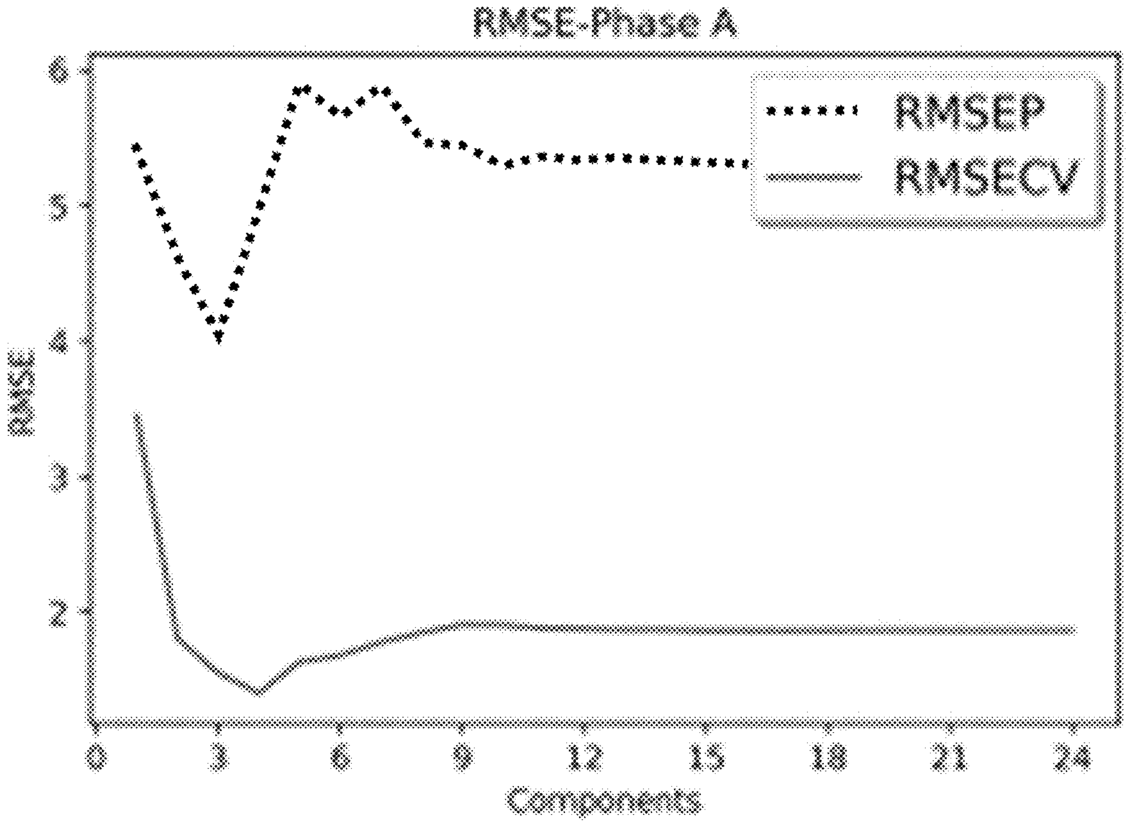
Figure 11D:
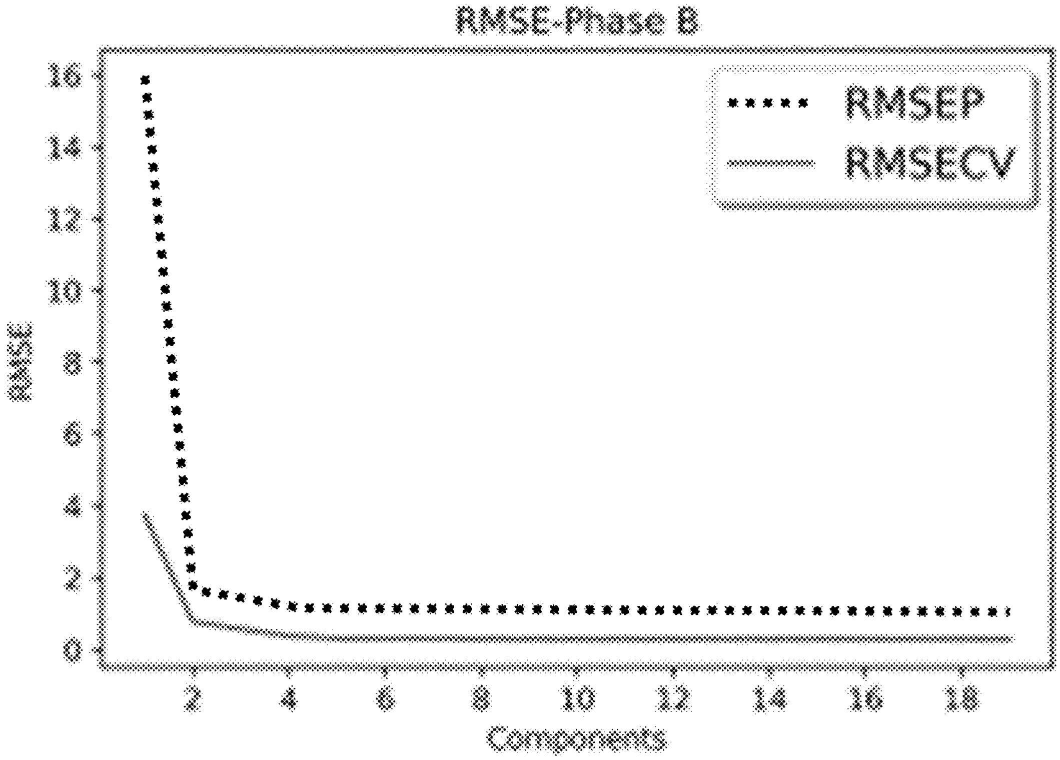

FIGS. 9A-9B FOM table displays the PSLR results of the analysis for 160 s. 11-fold Cross-Validation (CV) technique was applied to train the model to validate the model accuracy and its ability to generalize to unseen data. The $R^2$_CV (Cross-Validation) fit for the observed versus the predicted results is greater than 0.9 for both phase A and B while the RMSECV shows a low value (0.516 for phase A and 0.612 for phase B). The model was tested using the blind sample data. The $R^2$_P fit was found to be greater than 0.9 and the RMSEP (root mean square error of prediction) was found to be less than 1. This shows the developed model generalizes well to unseen data. One of the most important requirements of point-of-sale (POS) and process monitoring devices is the speed of analysis. To get a faster decision on the content of diesel adulteration, we trained the model on progressively smaller segments of the chromatographic data. By reducing the segment of the chromatogram used for building the model, a faster decision can be made on the sample content. We trained and tested the model on chromatographic data from the two phases in the range of 3.5 s to 160 s segments, respectively. FIGS. 9A-9D, 10A-10D, and 11A-11D show the results of 160 s, 40 s and 4 s analyses. The rest of the data is included in Table 1.

TABLE 1

The table lists results of PLS analysis for 3.5-160 s of the chromatograms

| TIME(S) | | PHASE A | PHASE B |
|---|---|---|---|
| 3.5 | $R^2$-P | 0.141 | 0.626 |
| | $R^2$-CV | 0.813 | 0.975 |
| | RMSEP | 3.785 | 2.496 |
| | RMSECV | 1.765 | 0.652 |
| | COMPONENT | 3 | 5 |
| 4 | $R^2$-P | 0.032 | 0.939 |
| | $R^2$-CV | 0.740 | 0.996 |
| | RMSEP | 4.018 | 1.012 |
| | RMSECV | 2.080 | 0.252 |
| | COMPONENT | 3 | 10 |
| 5 | $R^2$-P | 0.948 | 0.989 |
| | $R^2$-CV | 0.995 | 0.995 |
| | RMSEP | 0.934 | 0.437 |
| | RMSECV | 0.276 | 0.297 |
| | COMPONENT | 8 | 5 |

TABLE 1-continued

The table lists results of PLS analysis for 3.5-160 s of the chromatograms

| TIME(S) | | PHASE A | PHASE B |
|---|---|---|---|
| 10 | $R^2$-P | 0.989 | 0.85 |
| | $R^2$-CV | 0.997 | 0.995 |
| | RMSEP | 0.434 | 1.580 |
| | RMSECV | 0.235 | 0.293 |
| | COMPONENT | 6 | 4 |
| 20 | $R^2$-P | 0.988 | 0.994 |
| | $R^2$-CV | 0.997 | 0.998 |
| | RMSEP | 0.454 | 0.310 |
| | RMSECV | 0.206 | 0.181 |
| | COMPONENT | 4 | 4 |
| 40 | $R^2$-P | 0.983 | 0.988 |
| | $R^2$-CV | 0.998 | 0.998 |
| | RMSEP | 0.526 | 0.443 |
| | RMSECV | 0.183 | 0.173 |
| | COMPONENT | 3 | 8 |
| 80 | $R^2$-P | 0.986 | 0.986 |
| | $R^2$-CV | 0.995 | 0.998 |
| | RMSEP | 0.475 | 0.480 |
| | RMSECV | 0.298 | 0.193 |
| | COMPONENT | 2 | 9 |
| 120 | $R^2$-P | 0.979 | 0.984 |
| | $R^2$-CV | 0.991 | 0.997 |
| | RMSEP | 0.593 | 0.514 |
| | RMSECV | 0.398 | 0.214 |
| | COMPONENT | 4 | 8 |
| 160 | $R^2$-P | 0.984 | 0.978 |
| | $R^2$-CV | 0.954 | 0.995 |
| | RMSEP | 0.516 | 0.612 |
| | RMSECV | 0.872 | 0.297 |
| | COMPONENT | 3 | 6 |

Working with smaller segments of the chromatogram reduces the total information available to build the model. In our analysis, however, the data reduction was seen to have no major impact on model accuracy if more than 4 s of the chromatogram is used. The model for phase A fails for the first 4 s of chromatographic data showing a high RMSEP and RMSECV value and a $R^2$-P value of 0.032. For phase B, the model performance was good with $R^2$-P value of 0.939 and an RMSEP error of 1.012% (v/v). The data was not sufficient for accurate predictions of diesel purity at 3.5 s for Phase B. The results show that small segments chromatographic data can be used to determine diesel adulteration with kerosene. This method of analysis works well for diesel/kerosene blends because of the difference of boiling points of the major hydrocarbons of the two fuels. While kerosene is composed of lighter compounds, diesel is composed of heavier hydrocarbons. In adulterated diesel with kerosene, a more comprehensive GC analysis would show a higher ratio (FIGS. 14A-14B) of low boiling compounds compared to pure diesel. Taking the early segments of the chromatogram works because the low boilers are first to elute. The kerosene compounds can be used as a marker in the chromatograms for the detection of diesel purity. This method should also work for diesel adulteration with lighter organic solvents. In our analysis, Phase B outperforms Phase A for rapid detection even though it cannot generate well-separated peaks in the chromatographic data.

The data presented in this paper show that adulterated diesel with kerosene can be quantified with an RMSEP of ~1% (v/v) or less. Compared to other portable devices such as IROX 2000 which has a prediction error of less than 2% with a total analysis time of 3 minutes with the device warm up time of 10 minutes [3], our technique can reach a decision within seconds with less than a minute warm up time. Our approach also reduces system complexity in terms of computing hardware and memory (considering only the first few seconds of chromatographic data are needed). Refractometric detection methods while being the least complex suffer from temperature dependence issues. Compared to spectroscopic and refractometric methods which analyze the bulk content, our approach provides some separation of the sample thereby creating a chromatographic pattern with more information about the sample. This can lead to a more accurate quantitative analysis of the sample. Our technique matches the speed of detection (in the order of seconds) compared to aforementioned techniques.

Conclusion

This example demonstrates a system and a method that can detect 5% adulteration levels of kerosene in diesel in 4 s. In traditional GC analysis, partially resolved chromatograms are not vey useful in making an analytical observation on the chemical composition of a sample. This example shows that a partially resolved chromatogram coupled with chemometric techniques can qualify and quantify adulterated diesel with kerosene. This technique can be applied for a wide range of applications. Quality control and fraud detection in fuels can be performed using this technique. Using different column topologies, stationary phases and operating conditions on a portable platform, this technology can be applied rapidly in a wide variety of applications described herein. Multiple columns on one single device can reduce the footprint while eliminating the need for multiple injections and column multiplexing. On the analysis end, additional techniques such as data fusion of chromatograms from multiple columns can be used to improve the accuracy of the sensor. Fuel adulteration is not limited to diesel. Biodiesel, gasoline and ethanol are also some of the commonly adulterated fuels. However, the stationary phases used in this experiment may fail to discriminate those samples. One of the advantages of using RTILS is that they can be tuned with proper selectivity for the desired markers of the adulterated compounds [29]. Implementation of this method at POS and process control using μGCs can ensure online tracking of fuel quality.

References for Example 1

[1] I. Barra, M. A. Mansouri, M. Bousrabat, Y. Cherrah, A. Bouklouze, M. Kharbach, Discrimination and Quantification of Moroccan Gasoline Adulteration with Diesel Using Fourier Transform Infrared Spectroscopy and Chemometric Tools, J AOAC Int, 102(2019) 966-70.

[2] Y. Lawal, Kerosene Adulteration in Nigeria: Causes and Effects, American Journal of Social and Management Sciences, 2(2011) 371-6.

[3] L. Teixeira, F. Oliveira, H. Dossantos, P. Cordeiro, S. Almeida, Multivariate calibration in Fourier transform infrared spectrometry as a tool to detect adulterations in Brazilian gasoline, Fuel, 87(2008) 346-52.

[4] A. P. Gawande, J. P. Kaware, Fuel adulteration consequences in India: a review, Sci Revs Chem Commun, 3(2013) 161-71.

[5] R. Sharma, A. K. Gupta, Detection/estimation of adulteration in gasoline and diesel using ultrasonics, 2007 International Conference on Industrial and Information Systems, IEEE2007, pp. 509-12.

[6] R. Tharby, Catching Gasoline and Diesel Adulteration, 2002.

[7] R. Committee, Committee on Pricing and Taxation of Petroleum Products, 2006, February. URL: http://petroleum.nic.in/sites/default/files/Report1.pdf. Last accessed: 9/20/2020.

[8] B. Levitas, J. Matuzas, G. Viswanath, V. Basalingappa, V. Venkoparao, UWB based oil quality detection, 2011 IEEE International Conference on Ultra-Wideband (ICUWB), IEEE2011, pp. 220-4.

[9] T. Alvarez-Segura, J. Torres-Lapasio, C. Ortiz-Bolsico, M. Garcia-Alvarez-Coque, Stationary phase modulation in liquid chromatography through the serial coupling of columns: a review, Analytica chimica acta, 923(2016) 1-23.

[10] S. Kulkarni, S. Patrikar, Fiber optic detection of kerosene adulteration in petrol, International Conference on Photonics, Metamaterials & Plasmonics: Pmp-20192019.

[11] R. K. Verma, P. Suwalka, J. Yadav, Detection of adulteration in diesel and petrol by kerosene using SPR based fiber optic technique, Optical Fiber Technology, 43(2018) 95-100.

[12] B. P. Regmi, R. Chan, M. Agah, Ionic liquid functionalization of semi-packed columns for high-performance gas chromatographic separations, Journal of Chromatography A, 1510(2017) 66-72.

[13] J. Wang, J. Ma, E. T. Zellers, Room-temperature-ionic-liquid coated graphitized carbons for selective preconcentration of polar vapors, Journal of Chromatography A, 1609(2020) 460486.

[14] J. Sun, F. Guan, X. Zhu, Z. Ning, T. Ma, J. Liu, et al., Micro-fabricated packed gas chromatography column based on laser etching technology, Journal of Chromatography A, 1429(2016) 311-6.

[15] Y. Li, R. Zhang, T. Wang, Y. Wang, Y. Wang, L. Li, et al., A micro gas chromatography with separation capability enhanced by polydimethylsiloxane stationary phase functionalized by carbon nanotubes and graphene, Talanta, 154(2016) 99-108.

[16] L. Hou, F. Feng, W. You, P. Xu, F. Luo, B. Tian, et al., Pore size effect of mesoporous silica stationary phase on the separation performance of microfabricated gas chromatography columns, Journal of Chromatography A, 1552(2018) 73-8.

[17] B. Han, G. Wu, H. Huang, T. Liu, J. Wang, J. Sun, et al., A semi-packed micro GC column for separation of the NAFLD exhaled breath VOCs, Surface and Coatings Technology, 363(2019) 322-9.

[18] F. Luo, B. Zhao, F. Feng, L. Hou, W. You, P. Xu, et al., Improved separation of micro gas chromatographic column using mesoporous silica as a stationary phase support, Talanta, 188(2018) 546-51.

[19] B. P. Regmi, R. Chan, A. *Atta*, M. Agah, Ionic liquid-coated alumina-pretreated micro gas chromatography columns for high-efficient separations, Journal of Chromatography A, 1566(2018) 124-34.

[20] H. Shakeel, M. Agah, High density semipacked separation columns with optimized atomic layer deposited phases, Sensors and Actuators B: Chemical, 242(2017) 215-23.

[21] R. Chan, M. Agah, Semi-Packed Gas Chromatography Columns With Density Modulated Pillars, Journal of Microelectromechanical Systems, 28(2018) 114-24.

[22] H. Shakeel, D. Wang, J. R. Heflin, M. Agah, Improved self-assembled thiol stationary phases in microfluidic gas separation columns, Sensors and Actuators B: Chemical, 216(2015) 349-57.

[23] A. Garg, M. Akbar, E. Vejerano, S. Narayanan, L. Nazhandali, L. C. Marr, et al., Zebra GC: A mini gas chromatography system for trace-level determination of hazardous air pollutants, Sensors and Actuators B: Chemical, 212(2015) 145-54.

[24] J. Sun, N. Xue, W. Wang, H. Wang, C. Liu, T. Ma, et al., Compact prototype GC-PID system integrated with micro PC and micro GC column, Journal of Micromechanics and Microengineering, 29(2019) 035008.

[25] M. Akbar, D. Wang, R. Goodman, A. Hoover, G. Rice, J. R. Heflin, et al., Improved performance of micro-fabricated preconcentrators using silica nanoparticles as a surface template, J Chromatogr A, 1322(2013) 1-7.

[26] R. Bro, A. K. Smilde, Principal component analysis, Analytical Methods, 6(2014) 2812-31.

[27] S. Wold, M. Sjöström, L. Eriksson, PLS-regression: a basic tool of chemometrics, Chemometrics and intelligent laboratory systems, 58(2001) 109-30.

[28] E. Smit, S. De Goede, E. R. Rohwer, Class separation of the trace polar species present in diesel using hydrophilic interaction chromatography and high resolution mass spectrometry, Energy & Fuels, 32(2018) 8944-54.

[29] D. W. Armstrong, L. He, Y.-S. Liu, Examination of ionic liquids and their interaction with molecules, when used as stationary phases in gas chromatography, Analytical chemistry, 71(1999) 3873-6.

[30] B. Kanyathare, K. E. Peiponen, Hand-Held Refractometer-Based Measurement and Excess Permittivity Analysis Method for Detection of Diesel Oils Adulterated by Kerosene in Field Conditions, Sensors (Basel), 18(2018).

[31] V. Rawat, V. Nadkarni, S. N. Kale, High Sensitive Electrical Metamaterial Sensor for Fuel Adulteration Detection, Defence Science Journal, 66(2016).

[32] M. Bakir, M. Karaaslan, E. Unal, F. Karadag, F. Ö. Alkurt, O. Altintaş, et al., Microfluidic and Fuel Adulteration Sensing by Using Chiral Metamaterial Sensor, Journal of The Electrochemical Society, 165(2018) B475-B83.

[33] V. Mishra, V. Tiwari, P. N. Patel, Nanoporous Silicon Microcavity Based Fuel Adulteration Sensor, Silicon, 8(2015) 409-15.

[34] B. Kanyathare, K. E. Peiponen, Wavelength-dependent excess permittivity as indicator of kerosene in diesel oil, Appl Opt, 57(2018) 2997-3002.

[35] B. Kanyathare, K. Kuivalainen, J. Raty, P. Silfsten, P. Bawuah, K.-E. Peiponen, A prototype of an optical sensor for the identification of diesel oil adulterated by kerosene, Journal of the European Optical Society-Rapid Publications, 14(2018).

[36] G. C. Yadav, S. Prakash, G. Sharma, S. Kumar, V. Singh, Detection of kerosene adulteration in automobile fuel with a novel metal clad planar waveguide, Optics & Laser Technology, 119(2019).

[37] V. Mishra, S. C. Jain, N. Singh, G. Poddar, P. Kapur, Fuel adulteration detection using long period fiber grating sensor technology, (2008).

[38] R. Gotor, C. Tiebe, J. Schlischka, J. Bell, K. Rurack, Detection of Adulterated Diesel Using Fluorescent Test Strips and Smartphone Readout, Energy & Fuels, 31(2017) 11594-600.

[39] R. Leghrib, E. Ouacha, A. Zouida, B. Faiz, A. Amghar, Monitoring automobile fuel adulteration using ultrasound technique for environmental issues, Measurement, 150 (2020).

[40] N. C. Speller, N. Siraj, S. Vaughan, L. N. Speller, I. M. Warner, QCM virtual multisensor array for fuel discrimination and detection of gasoline adulteration, Fuel, 199 (2017) 38-46.

[41] N. K. L. Wiziack, L. G. Paterno, F. J. Fonseca, L. H. C. Mattoso, P. Gouma, A Combined Gas and Liquid Chemical Sensor Array for Fuel Adulteration Detection, 2011, pp. 178-9.

[42] J. Lee, S. Balakrishnan, J. Cho, S.-H. Jeon, J.-M. Kim, Detection of adulterated gasoline using colorimetric organic microfibers, Journal of Materials Chemistry, 21(2011).

It should be emphasized that the above-described aspects of the present disclosure are merely possible examples of implementations, and are set forth only for a clear understanding of the principles of the disclosure. Many variations and modifications may be made to the above-described aspects of the disclosure without departing substantially from the spirit and principles of the disclosure. All such modifications and variations are intended to be included herein within the scope of this disclosure.

I claim:

1. A micro gas chromatographic device for rapid detection of volatile organic compounds in a sample comprising a plurality of volatile organic compounds, the micro gas chromatographic device comprising:

a. a microfluidic separation column comprising a column inlet, wherein the microfluidic separation column is configured to provide partial or complete separation of the plurality of volatile organic compounds;

b. a plurality of capillaries, wherein each capillary in the plurality of capillaries is independently in fluid communication with the microfluidic separation column at a capillary inlet, and wherein each capillary in the plurality of capillaries has a capillary outlet opposite the capillary inlet, thereby maintaining separate flow paths for individual analytes or analyte groups post-separation; and c. a plurality of micro-detectors, wherein each micro-detector in the plurality of micro-detectors is independently positioned at or near the capillary outlet of a capillary in the plurality of capillaries and is configured to detect specific volatile compounds or compound classes passing through the capillary, enabling selective and parallel detection of the individual analytes or the analyte groups.

2. The micro gas chromatographic device according to claim 1, wherein the plurality of capillaries comprises from 2 to 10 capillaries.

3. The micro gas chromatographic device according to claim 1, wherein each capillary in the plurality of capillaries has a capillary length of about 50 cm to about 2.5 m.

4. The micro gas chromatographic device according to claim 3, wherein each capillary in the plurality of capillaries has a width of about 50 μm to about 500 μm.

5. The micro gas chromatographic device according to claim 4, wherein one or more capillaries in the plurality of capillaries comprises an array of micropillars.

6. The micro gas chromatographic device according to claim 5, wherein the array of micropillars has a geometry comprising one of a staggered semi-packed architecture or an unstaggered semi-packed architecture, in which each micropillar in the array of micropillars has a pitch size of about 5 μm to about 50 μm and a row spacing of about 10 μm to about 100 μm.

7. The micro gas chromatographic device according to claim 4, wherein one or more capillaries in the plurality of capillaries comprise one or more stationary phases selected from the group consisting of:

polyunsaturated hydrocarbons;
petroleum-based greases;
polysiloxanes;
polyalkylene glycols;
gold nanoparticles;
silica nanoparticles;
alumina;
ionic liquids;
metal organic frameworks; and
compounds having a structure according to the following formula

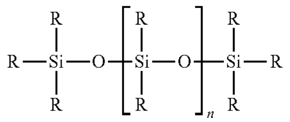

wherein n is an integer from 1 to 10 and each occurrence of R is independently selected from the group consisting of methyl, ethyl, phenyl, trifluoropropyl, $-C_3H_6CF$, cyanopropyl, and $-C_3H_6CN$.

8. The micro gas chromatographic device according to claim 1, wherein each micro-detector in the plurality of micro-detectors is independently selected from the group consisting of a μTCD detector, a μFID detector, a MOS gas sensor, a capacitive detector, a MPN chemiresistor, a SAW detector, a μPID detector, a μPlasma ionization detector, and a combination thereof.

9. The micro gas chromatographic device according to claim 1, wherein each capillary in the plurality of capillaries is distinct from each other in terms of one or more of a length, a width, a tortuosity, a presence of an array of micropillars, an arrangement of an array of micropillars, a surface functionalization, and a type of detector at or near the capillary outlet.

10. The micro gas chromatographic device according to claim 1, further comprising a sample port in fluid communication with a micro-pump and in fluid communication with the column inlet, wherein:

the micro-pump, in a first setting, is configured to draw a portion of the sample into the sample port; and the micro-pump, in a second setting, is configured to inject the portion of the sample into the column inlet.

11. The micro gas chromatographic device according to claim 1, further comprising one or more on-chip heaters and one or more temperature sensors to control a temperature in one or more capillary in the plurality of capillaries.

12. A method of making a gas chromatographic device according to claim 1, the method comprising:

a. applying a photoresist layer to a first surface of a silicon wafer to produce a mask layer;

b. patterning the mask layer using photolithography to produce a patterned mask layer defining at least the microfluidic separation column and the plurality of capillaries;

c. etching the silicon wafer having the patterned mask layer to produce an etched silicon wafer;

d. recleaning the etched silicon wafer; and e. bonding a lid on the first surface of the etched silicon wafer to form the microfluidic separation column and the plurality of capillaries.

13. The method according to claim 12, further comprising, in step (c), timing the etching to control a depth of the microfluidic separation column and the plurality of capillaries.

14. The method according to claim 12, wherein the silicon wafer comprises a silicon-on-insulator wafer comprising at least a wafer handle layer and a silicon oxide layer; and further comprising, in step (c), etching the wafer handle layer until reaching the silicon oxide layer to control a depth of the microfluidic separation column and plurality of capillaries.

15. The method according to claim 12, further comprising: a step (a') prior to step (c), step (a') comprising bonding a glass layer to a second surface of the silicon wafer opposite the first surface; and in step (c), etching the wafer to the glass layer to control a depth of the microfluidic separation column and the plurality of capillaries.

16. The method according to claim 12, further comprising functionalizing each capillary in the plurality of capillaries with a different stationary phase by pumping each of the different stationary phases into a different outlet in the plurality of capillaries.

17. A method of detecting one or more volatile organic compounds from a sample comprising a plurality of volatile organic compounds, the method comprising:

a. causing the sample to flow into the column inlet of the micro gas chromatographic device according to claim 1, whereby each of the one or more volatile organic compounds flows into one or more of the capillary inlets; and b. measuring a signal at one or more micro-detectors in the plurality of micro-detectors, wherein the signal is indicative of a presence or an absence of a specific volatile organic compound in the plurality of volatile organic compounds.

18. The method according to claim 17, wherein the micro gas chromatographic device comprises a sample port in fluid communication with a micro-pump and in fluid communication with the column inlet; and further comprising:

placing the micro-pump in a first setting to draw a portion of the sample into the sample port; and placing the micro-pump in a second setting to inject the portion of the sample into the column inlet.

19. The method according to claim 17, further comprising controlling one or more of (i) a flow rate of a carrier gas flowing into the column inlet, (ii) a temperature of a specific capillary in the plurality of capillaries, and (iii) a time period during which signals are detected at the one or more micro-detectors.

20. The method according to claim 19, further comprising one or more of (i) a principal component analysis and (ii) a partial least squares regression over the signals from the one or more micro-detectors for a period of time.

* * * * *